(12) United States Patent
Shelton, IV et al.

(10) Patent No.: US 8,419,635 B2
(45) Date of Patent: Apr. 16, 2013

(54) SURGICAL ACCESS DEVICE HAVING REMOVABLE AND REPLACEABLE COMPONENTS

(75) Inventors: Frederick E. Shelton, IV, Hillsboro, OH (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 544 days.

(21) Appl. No.: 12/420,202

(22) Filed: Apr. 8, 2009

(65) Prior Publication Data

US 2010/0262080 A1    Oct. 14, 2010

(51) Int. Cl.
*A61B 1/32* (2006.01)

(52) U.S. Cl.
USPC .......................................................... 600/208

(58) Field of Classification Search .................. 606/201, 606/203–205, 208, 210, 235; 604/164.01, 604/164.04, 164.07, 164.09, 164.11, 165.01, 604/165.02
See application file for complete search history.

(56) References Cited

U.S. PATENT DOCUMENTS

| | | | |
|---|---|---|---|
| 2,129,391 | A | 9/1938 | Wappler |
| 3,402,710 | A | 9/1968 | Paleschuck |
| 3,654,965 | A | 4/1972 | Gramain |
| 4,112,932 | A | 9/1978 | Chiulli |
| 4,306,545 | A | 12/1981 | Ivan et al. |
| 4,379,458 | A | 4/1983 | Bauer et al. |
| 4,402,683 | A | 9/1983 | Kopman |
| 4,417,888 | A | 11/1983 | Cosentino et al. |
| 5,010,925 | A | 4/1991 | Atkinson et al. |
| 5,091,435 | A | 2/1992 | Suzuki et al. |
| 5,183,471 | A | 2/1993 | Wilk |
| 5,197,955 | A | 3/1993 | Stephens et al. |
| 5,207,213 | A | 5/1993 | Auhll et al. |
| 5,209,737 | A | 5/1993 | Ritchart et al. |
| 5,209,741 | A | 5/1993 | Spaeth |
| 5,235,966 | A | 8/1993 | Jamner |

(Continued)

FOREIGN PATENT DOCUMENTS

| | | |
|---|---|---|
| DE | 19814576 A1 | 10/1999 |
| DE | 20022005 U1 | 4/2001 |

(Continued)

OTHER PUBLICATIONS

U.S. Appl. No. 12/242,333, filed Sep. 30, 2008.
U.S. Appl. No. 12/242,353, filed Sep. 30, 2008.
U.S. Appl. No. 12/242,381, filed Sep. 30, 2008.
U.S. Appl. No. 12/242,711, filed Sep. 30, 2008.
U.S. Appl. No. 12/242,721, filed Sep. 30, 2008.
U.S. Appl. No. 12/242,726, filed Sep. 30, 2008.
U.S. Appl. No. 12/242,765, filed Sep. 30, 2008.

(Continued)

*Primary Examiner* — Cris L Rodriguez
*Assistant Examiner* — Eric Rosen

(57) ABSTRACT

Methods and devices are provided to improve access to a surgical site during surgical procedures. In one exemplary embodiment a surgical access device is provided having a cannula, a cannula base, and a retractor. The cannula base is configured to couple both to the retractor and the cannula to provide access to a surgical site. The cannula can be removably and replaceably coupled to the cannula base. Optionally, the cannula base can be removably and replaceably coupled to the retractor. As desired, the cannula can be decoupled from the cannula base, which can allow for an object to be removed from the surgical site and/or for the cannula, or another cannula to be attached to the cannula base that remains in place to maintain access to the surgical site. Exemplary methods for accessing a surgical site are also provided.

15 Claims, 15 Drawing Sheets

U.S. PATENT DOCUMENTS

| | | | |
|---|---|---|---|
| 5,269,772 | A | 12/1993 | Wilk |
| 5,308,336 | A | 5/1994 | Hart et al. |
| 5,312,417 | A | 5/1994 | Wilk |
| 5,320,611 | A | 6/1994 | Bonutti et al. |
| 5,342,315 | A | 8/1994 | Rowe et al. |
| 5,366,478 | A | 11/1994 | Brinkerhoff et al. |
| 5,385,553 | A | 1/1995 | Hart et al. |
| 5,385,560 | A | 1/1995 | Wulf |
| 5,391,154 | A | 2/1995 | Young |
| 5,431,676 | A | 7/1995 | Dubrul et al. |
| 5,443,452 | A | 8/1995 | Hart et al. |
| 5,443,484 | A | 8/1995 | Kirsch et al. |
| 5,476,475 | A | 12/1995 | Gadberry |
| 5,480,410 | A | 1/1996 | Cuschieri et al. |
| 5,531,758 | A | 7/1996 | Uschold et al. |
| 5,545,179 | A | 8/1996 | Williamson, IV |
| 5,562,677 | A | 10/1996 | Hildwein et al. |
| 5,569,205 | A | 10/1996 | Hart et al. |
| 5,569,254 | A | 10/1996 | Carlson et al. |
| 5,584,850 | A | 12/1996 | Hart et al. |
| 5,628,732 | A | 5/1997 | Antoon, Jr. et al. |
| 5,634,911 | A | 6/1997 | Hermann et al. |
| 5,634,937 | A | 6/1997 | Mollenauer et al. |
| 5,643,301 | A | 7/1997 | Mollenauer |
| 5,653,705 | A | 8/1997 | de la Torre et al. |
| 5,653,718 | A | 8/1997 | Yoon |
| 5,672,168 | A | 9/1997 | de la Torre et al. |
| 5,676,657 | A | 10/1997 | Yoon |
| 5,695,448 | A | 12/1997 | Kimura et al. |
| 5,707,359 | A | 1/1998 | Bufalini |
| 5,752,970 | A | 5/1998 | Yoon |
| 5,782,812 | A | 7/1998 | Hart et al. |
| 5,797,888 | A | 8/1998 | Yoon |
| 5,803,919 | A | 9/1998 | Hart et al. |
| 5,814,058 | A | 9/1998 | Carlson et al. |
| 5,827,319 | A | 10/1998 | Carlson et al. |
| 5,843,040 | A | 12/1998 | Exline |
| 5,865,807 | A | 2/1999 | Blake, III |
| 5,868,762 | A | 2/1999 | Cragg et al. |
| 5,882,344 | A | 3/1999 | Stouder, Jr. |
| 5,891,013 | A | 4/1999 | Thompson |
| 5,899,208 | A | 5/1999 | Bonadio |
| 5,906,577 | A | 5/1999 | Beane et al. |
| 5,946,280 | A | 8/1999 | Ohkubo |
| 5,957,913 | A | 9/1999 | de la Torre et al. |
| 5,990,382 | A | 11/1999 | Fox |
| 5,997,515 | A | 12/1999 | de la Torre et al. |
| 6,024,736 | A | 2/2000 | de la Torre et al. |
| RE36,702 | E | 5/2000 | Green et al. |
| 6,056,766 | A | 5/2000 | Thompson et al. |
| 6,066,090 | A | 5/2000 | Yoon |
| 6,077,288 | A | 6/2000 | Shimomura et al. |
| 6,080,174 | A | 6/2000 | Dubrul et al. |
| 6,086,603 | A | 7/2000 | Termin et al. |
| 6,120,513 | A | 9/2000 | Bailey et al. |
| 6,123,689 | A | 9/2000 | To et al. |
| 6,142,396 | A | 11/2000 | Gallus |
| 6,142,936 | A | 11/2000 | Beane et al. |
| 6,162,196 | A | 12/2000 | Hart et al. |
| 6,217,555 | B1 | 4/2001 | Hart et al. |
| 6,245,052 | B1 | 6/2001 | Orth et al. |
| 6,258,069 | B1 | 7/2001 | Carpentier et al. |
| 6,277,064 | B1 | 8/2001 | Yoon |
| 6,315,770 | B1 | 11/2001 | de la Torre et al. |
| 6,319,246 | B1 | 11/2001 | de la Torre et al. |
| 6,325,812 | B1 | 12/2001 | Dubrul et al. |
| 6,348,034 | B1 | 2/2002 | Thompson |
| 6,352,503 | B1 | 3/2002 | Matsui et al. |
| 6,440,061 | B1 | 8/2002 | Wenner et al. |
| 6,440,063 | B1 | 8/2002 | Beane et al. |
| 6,447,489 | B1 | 9/2002 | Peterson |
| 6,454,783 | B1 | 9/2002 | Piskun |
| 6,458,077 | B1 | 10/2002 | Boebel et al. |
| 6,488,620 | B1 | 12/2002 | Segermark et al. |
| 6,551,270 | B1 | 4/2003 | Bimbo et al. |
| 6,551,282 | B1 | 4/2003 | Exline et al. |
| 6,589,167 | B1 | 7/2003 | Shimomura et al. |
| 6,605,063 | B2 | 8/2003 | Bousquet |
| 6,669,674 | B1 | 12/2003 | Macoviak et al. |
| 6,702,787 | B2 | 3/2004 | Racenet et al. |
| 6,706,033 | B1 | 3/2004 | Martinez et al. |
| 6,706,050 | B1 | 3/2004 | Giannadakis |
| 6,908,430 | B2 | 6/2005 | Caldwell et al. |
| 6,939,296 | B2 | 9/2005 | Ewers et al. |
| 6,945,932 | B1 | 9/2005 | Caldwell et al. |
| 6,972,026 | B1 | 12/2005 | Caldwell et al. |
| 7,014,628 | B2 | 3/2006 | Bousquet |
| 7,052,454 | B2 | 5/2006 | Taylor |
| 7,083,626 | B2 | 8/2006 | Hart et al. |
| 7,118,528 | B1 | 10/2006 | Piskun |
| 7,163,510 | B2 | 1/2007 | Kahle et al. |
| 7,163,525 | B2 | 1/2007 | Franer |
| 7,214,185 | B1 | 5/2007 | Rosney et al. |
| 7,229,408 | B2 | 6/2007 | Douglas et al. |
| 7,338,473 | B2 | 3/2008 | Campbell et al. |
| 7,344,547 | B2 | 3/2008 | Piskun |
| 7,371,227 | B2 | 5/2008 | Zeiner |
| 7,393,322 | B2 | 7/2008 | Wenchell |
| 7,449,011 | B2 | 11/2008 | Wenchell et al. |
| 7,481,795 | B2 | 1/2009 | Thompson et al. |
| 8,012,088 | B2 * | 9/2011 | Butler et al. ................. 600/208 |
| 2002/0156432 | A1 | 10/2002 | Racenet et al. |
| 2003/0028179 | A1 | 2/2003 | Piskun |
| 2003/0139756 | A1 | 7/2003 | Brustad |
| 2003/0216770 | A1 | 11/2003 | Persidsky et al. |
| 2004/0015185 | A1 | 1/2004 | Ewers et al. |
| 2004/0019322 | A1 | 1/2004 | Hoffmann |
| 2004/0082969 | A1 | 4/2004 | Kerr |
| 2004/0106942 | A1 | 6/2004 | Taylor et al. |
| 2004/0117032 | A1 | 6/2004 | Roth |
| 2004/0138528 | A1 | 7/2004 | Richter et al. |
| 2004/0199121 | A1 | 10/2004 | Wenchell et al. |
| 2004/0215063 | A1 | 10/2004 | Bonadio et al. |
| 2004/0230160 | A1 | 11/2004 | Blanco |
| 2004/0230161 | A1 | 11/2004 | Zeiner |
| 2004/0254426 | A1 | 12/2004 | Wenchell |
| 2005/0020884 | A1 | 1/2005 | Hart et al. |
| 2005/0033342 | A1 | 2/2005 | Hart et al. |
| 2005/0085842 | A1 | 4/2005 | Eversull et al. |
| 2005/0137609 | A1 | 6/2005 | Guiraudon |
| 2005/0148823 | A1 | 7/2005 | Vaugh et al. |
| 2005/0155611 | A1 | 7/2005 | Vaugh et al. |
| 2005/0192483 | A1 | 9/2005 | Bonadio et al. |
| 2005/0209608 | A1 | 9/2005 | O'Heeron |
| 2005/0215862 | A1 | 9/2005 | Larson et al. |
| 2005/0216028 | A1 | 9/2005 | Hart et al. |
| 2005/0222582 | A1 | 10/2005 | Wenchell |
| 2005/0267419 | A1 | 12/2005 | Smith |
| 2005/0273132 | A1 | 12/2005 | Shluzas et al. |
| 2005/0277946 | A1 | 12/2005 | Greenhalgh |
| 2006/0012965 | A1 | 1/2006 | Beall et al. |
| 2006/0019592 | A1 | 1/2006 | Kupferberg et al. |
| 2006/0019723 | A1 | 1/2006 | Vorenkamp et al. |
| 2006/0020241 | A1 | 1/2006 | Piskun et al. |
| 2006/0020281 | A1 | 1/2006 | Smith |
| 2006/0021061 | A1 | 1/2006 | Cerri et al. |
| 2006/0021891 | A1 | 2/2006 | Franer et al. |
| 2006/0025813 | A1 | 2/2006 | Shelton et al. |
| 2006/0030755 | A1 | 2/2006 | Ewers et al. |
| 2006/0071432 | A1 | 4/2006 | Staudner |
| 2006/0129165 | A1 | 6/2006 | Edoga et al. |
| 2006/0212061 | A1 | 9/2006 | Wenchell |
| 2006/0212062 | A1 | 9/2006 | Farascioni |
| 2006/0217665 | A1 | 9/2006 | Prosek |
| 2006/0224129 | A1 | 10/2006 | Beasley et al. |
| 2006/0224164 | A1 | 10/2006 | Hart et al. |
| 2006/0229501 | A1 | 10/2006 | Jensen et al. |
| 2006/0241651 | A1 | 10/2006 | Wilk |
| 2006/0241671 | A1 | 10/2006 | Greenhalgh |
| 2006/0247498 | A1 | 11/2006 | Bonadio et al. |
| 2006/0247500 | A1 | 11/2006 | Voegele et al. |
| 2006/0247516 | A1 | 11/2006 | Hess et al. |
| 2006/0247586 | A1 | 11/2006 | Voegele et al. |
| 2006/0247673 | A1 | 11/2006 | Voegele et al. |
| 2006/0247678 | A1 | 11/2006 | Weisenburgh et al. |
| 2006/0258899 | A1 | 11/2006 | Gill et al. |
| 2006/0264706 | A1 | 11/2006 | Piskun |

| | | | |
|---|---|---|---|
| 2006/0270911 A1 | 11/2006 | Voegele et al. | |
| 2007/0049966 A1 | 3/2007 | Bonadio et al. | |
| 2007/0060939 A1 | 3/2007 | Lancial et al. | |
| 2007/0085232 A1 | 4/2007 | Brustad et al. | |
| 2007/0088202 A1 | 4/2007 | Albrecht et al. | |
| 2007/0088204 A1 | 4/2007 | Albrecht et al. | |
| 2007/0088258 A1 | 4/2007 | Wenchell et al. | |
| 2007/0088277 A1 | 4/2007 | McGinley et al. | |
| 2007/0118021 A1 | 5/2007 | Pokorney | |
| 2007/0118175 A1 | 5/2007 | Butler et al. | |
| 2007/0151566 A1 | 7/2007 | Kahle et al. | |
| 2007/0185453 A1 | 8/2007 | Michael et al. | |
| 2007/0208312 A1 | 9/2007 | Norton et al. | |
| 2007/0255219 A1 | 11/2007 | Vaugh et al. | |
| 2008/0009797 A1 | 1/2008 | Stellon et al. | |
| 2008/0025519 A1 | 1/2008 | Yu et al. | |
| 2008/0027476 A1 | 1/2008 | Piskun | |
| 2008/0051739 A1 | 2/2008 | McFarlane | |
| 2008/0058728 A1 | 3/2008 | Soltz et al. | |
| 2008/0065021 A1 | 3/2008 | Jenkins et al. | |
| 2008/0086080 A1 | 4/2008 | Mastri et al. | |
| 2008/0119821 A1 | 5/2008 | Agnihotri et al. | |
| 2008/0132765 A1 | 6/2008 | Beckman et al. | |
| 2008/0249371 A1* | 10/2008 | Beckman et al. | 600/204 |
| 2008/0255519 A1 | 10/2008 | Piskun et al. | |
| 2008/0281161 A1 | 11/2008 | Albrecht et al. | |
| 2009/0005799 A1 | 1/2009 | Franer et al. | |
| 2009/0082731 A1 | 3/2009 | Moreno | |
| 2009/0118587 A1 | 5/2009 | Voegele et al. | |
| 2009/0187079 A1 | 7/2009 | Albrecht et al. | |
| 2009/0270685 A1 | 10/2009 | Moreno et al. | |
| 2009/0270686 A1 | 10/2009 | Duke et al. | |
| 2009/0270818 A1 | 10/2009 | Duke | |
| 2010/0010310 A1 | 1/2010 | Weisenburgh, II et al. | |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0228090 A1 | 9/2010 | Weisenburgh, II et al. | |
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0228096 A1 | 9/2010 | Weisenburgh, II et al. | |
| 2010/0228198 A1 | 9/2010 | Widenhouse et al. | |
| 2010/0249525 A1 | 9/2010 | Shelton, IV et al. | |
| 2010/0261970 A1 | 10/2010 | Shelton, IV et al. | |
| 2010/0261972 A1 | 10/2010 | Widenhouse et al. | |
| 2010/0261974 A1 | 10/2010 | Shelton, IV et al. | |
| 2010/0262080 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0280327 A1 | 11/2010 | Nobis et al. | |
| 2010/0312060 A1 | 12/2010 | Widenhouse et al. | |
| 2010/0312061 A1 | 12/2010 | Hess et al. | |
| 2010/0312062 A1 | 12/2010 | Cropper et al. | |
| 2010/0312063 A1 | 12/2010 | Hess et al. | |
| 2010/0312064 A1 | 12/2010 | Weisenburgh, II et al. | |
| 2010/0312065 A1 | 12/2010 | Shelton, IV et al. | |
| 2010/0312066 A1 | 12/2010 | Cropper et al. | |
| 2010/0312189 A1 | 12/2010 | Shelton, IV et al. | |

FOREIGN PATENT DOCUMENTS

| | | |
|---|---|---|
| EP | 568383 A1 | 11/1993 |
| EP | 577400 A1 | 1/1994 |
| EP | 0637431 A1 | 2/1995 |
| EP | 646358 A1 | 4/1995 |
| EP | 709918 | 5/1996 |
| EP | 0776231 B1 | 6/1997 |
| EP | 950376 | 10/1999 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1702575 A2 | 9/2006 |
| EP | 1731105 A1 | 12/2006 |
| EP | 1774918 A1 | 4/2007 |
| EP | 2119404 A1 | 11/2009 |
| FR | 2710270 A1 | 3/1995 |
| JP | 2006320750 | 11/2006 |
| WO | 9407552 | 4/1994 |
| WO | 9407552 A1 | 4/1994 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | 0032263 A1 | 6/2000 |
| WO | 0041759 A1 | 7/2000 |
| WO | 0108563 A2 | 2/2001 |
| WO | 0217800 A2 | 3/2002 |
| WO | 2004030515 A2 | 4/2004 |
| WO | 2005000454 A1 | 1/2005 |
| WO | 2005002454 A1 | 1/2005 |
| WO | 2005087112 A1 | 9/2005 |
| WO | 2005094432 A2 | 10/2005 |
| WO | 2005097019 A2 | 10/2005 |
| WO | 2005097234 A2 | 10/2005 |
| WO | 2006057982 A2 | 6/2006 |
| WO | 2007008741 A1 | 1/2007 |
| WO | 2007119232 A2 | 10/2007 |
| WO | 2008024502 A2 | 2/2008 |
| WO | 2008028149 A2 | 3/2008 |
| WO | 2008121294 A1 | 10/2008 |
| WO | 2009035663 A2 | 3/2009 |

OTHER PUBLICATIONS

U.S. Appl. No. 12/399,482, filed Mar. 6, 2009.
U.S. Appl. No. 12/399,547, filed Mar. 6, 2009.
U.S. Appl. No. 12/399,625, filed Mar. 6, 2009.
U.S. Appl. No. 12/420,107, filed Apr. 8, 2009.
U.S. Appl. No. 12/420,232, filed Apr. 8, 2009.
U.S. Appl. No. 12/420,146, filed Apr. 8, 2009.
International Search Report and Written Opinion for International App. No. PCT/US2010/036811 dated Sep. 14, 2010 (6 pages).
International Search Report, from PCT/US10/36829, mailed Sep. 9, 2010 (5 pages).
European Search Report, EP 10250732, dated Jul. 28, 2010.
International Search Report and Written Opinion for Application No. PCT/US2010/037190, dated Sep. 22, 2010 (15 pages).
"Surgeon performs single-port laparoscopic surgery > Kidney removal with instructions inserted through single port access SPA > One Port Umbilicus Surgery OPUS > Uretero-pelvic junction repair> Bilateral pyeloplasy > Triport > Quadport > R-Port laparoscopic access device > Advanced Surgical Concepts ASC" Ideas for Surgery.com, Dec. 2007, 4 pages.
Desai, Mihir M. et al., "Laparoscopic and Robtic Urology—Scarless single port transumbilical nephrectomy and pyeloplasty: first clinical report," Journal Compilation, 2008 BJU International, 101, pp. 83-88.
Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.
Nakajima K, et al. Hand-assisted laparoscopic colorectal surgery using GelPort, Surg Endosc. Jan. 2004; 18(1)102-5. Epub Sep. 10, 2003.
Nakajima K, et al. Use of the surgical towel in colorectal hand-assisted laparoscopic surgery (HALS), Surg Endosc. Mar. 2004; 18(3):552-3.
Patel, R. et al. "Hand-Assisted Laparoscopic Devices: The Second Generation," Journal of Endourology, vol. 18, No. 7, Sep. 2004, pp. 649-653.
Rane, A. et al., "Single-Port Access Nephrectomy and Other Laparoscopic Urologic Procedures Using a Novel Laparoscopic Port (R-Port)," Urology, Aug. 2008; 72(2):260-264.
International Search Report and Written Opinion for Application No. PCT/US2010/036806, dated Sep. 3, 2010 (8 pages).
International Search Report and Written Opinion for Application No. PCT/US2010/036820, dated Oct. 22, 2010 (18 pages).

* cited by examiner

SURGICAL ACCESS DEVICE HAVING REMOVABLE AND REPLACEABLE COMPONENTS

FIELD

The present invention relates to methods and devices for accessing a surgical site, and more particularly to methods and devices for introducing multiple instruments into a body cavity through a single incision.

BACKGROUND

Minimally invasive surgical techniques such as endoscopies and laparoscopies are often preferred over traditional open surgeries because the recovery time, pain, and surgery-related complications are typically less with minimally invasive surgical techniques. In many laparoscopic procedures, the abdominal cavity is insufflated with carbon dioxide gas to a pressure of approximately 15 mm Hg. The abdominal wall is pierced and a cannula or trocar that is approximately 5 to 10 mm in diameter is inserted into the abdominal cavity. Typically multiple cannulas or trocars are inserted and placed at the surgical site so multiple instruments, such as laparoscopic telescopes, graspers, dissectors, scissors, retractors, etc., can be used at the same time. While miniaturized versions of laparoscopic procedures have also been developed, the instruments for such procedures are generally more expensive and fragile, and still typically require the use of multiple instruments or channels that have diameters of about 2 to 3 mm.

Because of the rise in popularity of minimally invasive surgeries, there has been significant development with respect to the procedures and the instruments used in such procedures. For example, in some procedures a single incision at the navel can be sufficient to provide access to a surgical site. This is because the umbilicus can be a preferred way to access an abdominal cavity in a laparoscopic procedure. The umbilical incision can be easily enlarged without significantly compromising cosmesis and without significantly increasing the chances of wound complications, thus allowing multiple instruments to be introduced through a single incision. However, a "chopstick" effect can occur which causes interference between the surgeon's hands and the instruments. This interference greatly reduces the surgeon's ability to perform a desired procedure.

Some surgical access devices have been developed to try and reduce the "chopstick effect." For example, a device can include a chamber having a plurality of separate sealing channels that are configured to access a surgical location. Each sealing channel can be configured to receive an instrument and can seal the outside environment from the surgical location. Current devices designed to alleviate the "chopstick effect," however, have their own unique problems. The configurations of these assemblies can lead to problems such as tissue collapsing around channels formed in the cannula. For example, the fascia layer of the abdomen can collapse around the channels when the cannula is used in conjunction with an abdominal procedure. The channels can be working channels in which instruments are often disposed, and thus the collapsed tissue can restrict and inhibit independent motion of the instruments disposed in the cannula. This problem is often exacerbated as the number of instruments disposed through the cannula increases.

Further, because insufflation is generally used as part of laparoscopic procedures, a resulting force is applied to the cannula that causes the cannula to be undesirably pushed in a direction out of a body, like a cork in a pressurized liquid bottle. While the assemblies can generally be sutured in place, the retention and stability capabilities of such assemblies are weak. Additionally, because the cannula is sutured to the tissue, removing the cannula during the course of the surgical procedure is both difficult and inconvenient. Thus, a surgeon is typically unable to easily remove objects from the surgical site or to use different types of cannulas during a single procedure.

Accordingly, there is a need for improved methods and devices for accessing a surgical site during a laparoscopic procedure. There is additionally a need for procedures and devices that allow for a cannula to be easily removed from a surgical site and replaced or reattached during a surgical procedure.

SUMMARY

Methods and devices are generally provided to improve a surgeon's access to a body during surgical procedures, such as laparoscopies. In one embodiment a surgical access device includes a cannula, a cannula base configured to seat the cannula such that the cannula is removable and replaceable, and a retractor coupled to and extending distally from the cannula base. The cannula can have a proximal opening that is in communication with a plurality of separate and distinct distal passageways. In one embodiment the cannula base and the retractor are fixedly coupled to one another. In another embodiment the cannula base is removable from the retractor, and thus can be replaced, for example, by another cannula base. When the cannula base and the retractor are coupled together, a fluid-tight configuration can be formed. In one embodiment, the retractor is more flexible than the cannula base. The retractor can be configured to form a pathway through tissue, and in one embodiment it can include a distal ring. The distal ring can have a diameter that is greater than a diameter of a proximal portion of the retractor. In another embodiment multiple cannulas can be configured to be removably and replaceably coupled to the cannula base.

The removable and replaceable nature of the cannula with respect to the cannula base can be accomplished in a variety of manners, but preferably a fluid-tight mating connection is formed between the two components. For example, the cannula can include a threaded section that is configured to mate with a threaded section on the cannula base. Such a configuration will allow the cannula and cannula base to be removably and replaceably coupled. Another example of a mating configuration includes the cannula base having at least one receiving portion and the cannula having at least one protrusion. The protrusion(s) of the cannula can be configured to extend into and engage the receiving portion(s) of the cannula base. Such a configuration can also result in the cannula and cannula base being removably and replaceably coupled. These mating techniques, as well as various other techniques known in the art, can likewise be used to removably and replaceably mate the retractor and the cannula base.

In another embodiment of a surgical access device, the device includes a cannula having an opening extending through the cannula between the proximal and distal ends of the cannula and a support base configured to removably seat the cannula. The cannula can include a plurality of elongate flexible channels that extend distally from the proximal end and through a retractor of the surgical access device. Each channel can have an opening extending through the channel and in communication with the opening that extends through the cannula. The retractor can extend distally from the support base. The support base can optionally be removably and replaceably coupled to the retractor. When the cannula base and the retractor are coupled together, a fluid-tight configuration can be formed. In one embodiment either the support base or cannula includes a male locking mechanism that is configured to couple with a female locking mechanism located on the other of the support base and cannula. This can allow the support base and cannula to be removably and replaceably coupled. In another embodiment either the support base or retractor includes a male locking mechanism that is configured to couple with a female locking mechanism located on the other of the support base and retractor. This can allow the support base and retractor to be removably and replaceably coupled. In one embodiment the retractor can include a distal ring that has a diameter greater than a diameter of a proximal portion of the retractor.

In one embodiment of a method for accessing a surgical site, a retractor is positioned through an opening in tissue such that the retractor forms a working channel extending into a body cavity. A cannula can be seated in a cannula base that extends proximally from a proximal end of the retractor. This can allow a seal to be formed between the cannula and the cannula base. An instrument can be inserted through the cannula and through one of a plurality of separate and distinct sealing channels that extend distally from the cannula. This can allow a distal end of the instrument to be positioned within the body cavity. In one embodiment proximal and distal portions of the retractor engage the tissue surrounding the opening between the proximal and distal portions. In another embodiment, at least a portion of the cannula base Is disposed within the opening in tissue. Optionally, the cannula can be removed from the cannula base and a second cannula can be seated in the cannula base. This can allow a seal to be formed between the second cannula and the cannula base. Seating the cannula in the cannula base can be performed in a variety of manners, for example by threading the cannula into the cannula base. The method can also include inserting a second instrument through another one of the plurality of sealing channels to allow a distal end of the second instrument to enter the body cavity. In one embodiment the method further includes removing the cannula and removing an object from the body cavity through the retractor and cannula base.

BRIEF DESCRIPTION OF DRAWINGS

This invention will be more fully understood from the following detailed description taken in conjunction with the accompanying drawings, in which.

DETAILED DESCRIPTION

Figure 1:
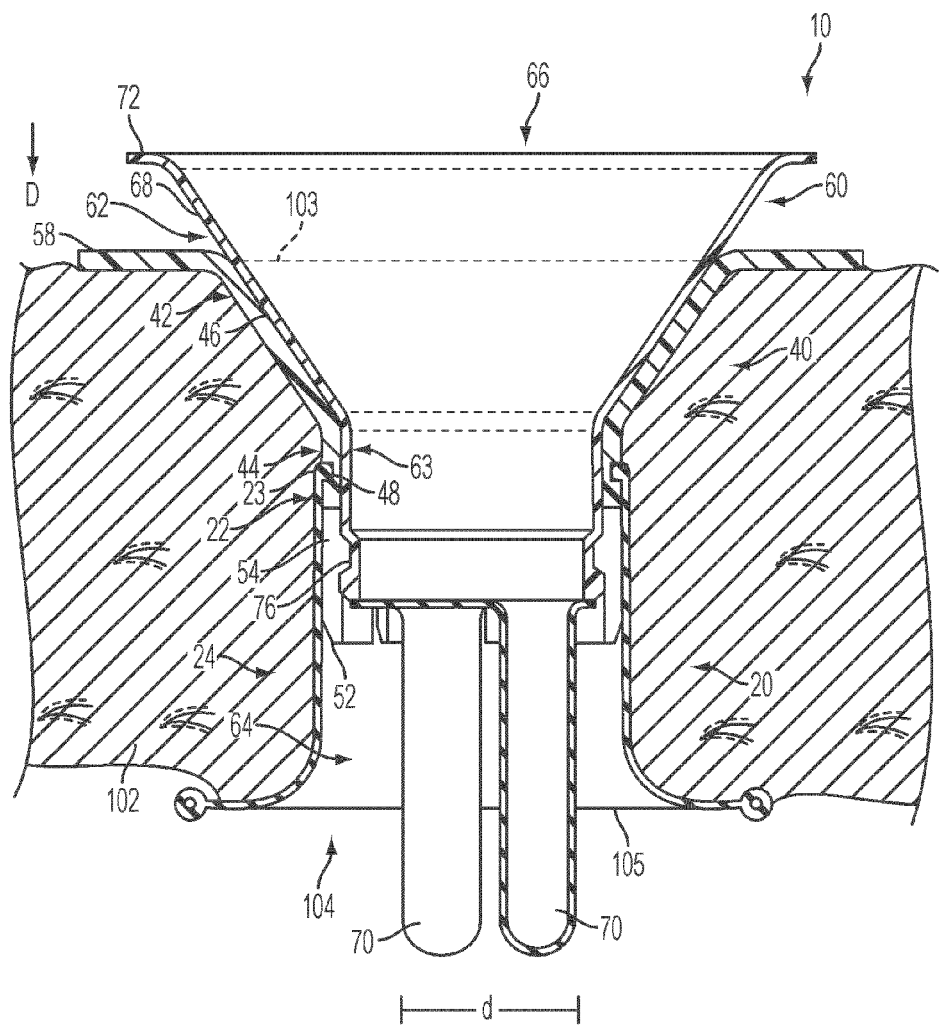
FIG. 1 is a side cross-sectional view of one exemplary embodiment of a surgical access device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. A person skilled in the art will also recognize that to the extent that the dimensions disclosed herein are described with respect to a radius or diameter that is typically used to describe circular or cylindrical elements, equivalent measurements for components that are a different geometric shape can be easily determined. Likewise, a person skilled in the art will recognize that to the extent particular materials are discussed as having particular properties, such as being rigid or flexible, other materials can also be used, and further, materials can be treated in particular ways to make them more rigid or more flexible as desired.

A surgical access device is generally provided for minimally-invasive surgeries such as laparoscopic surgeries. The surgical access device can be disposed in a body to allow for access to a surgical site from outside of the body. The device can generally be configured to receive one or more instruments through the device so that the instruments can be used to perform a desired procedure. The device can have a number of different components, but in an exemplary embodiment shown in FIG. 1, a device 10 includes a retractor 20, a cannula base 40, and a cannula 60. In such an embodiment the retractor 20 can be configured to be disposed in an incision 104 formed through tissue 102 to form a working channel extending through the tissue 102 and into a body cavity. The cannula base 40 can be coupled to the retractor 20, and the cannula 60 can be coupled to the cannula base 40. Access to the body can be gained through the cannula 60, and thus through the cannula base 40 and the retractor 20.

In an exemplary embodiment of the surgical access device 10, the cannula 60 and cannula base 40 can be removably and replaceably coupled such that the cannula 60 can be attached and detached from the cannula base 40 as desired and/or other cannulas can be attached and detached as desired. In other embodiments the cannula base 40 and the retractor 20 can be removably and replaceably coupled in a similar manner. It can be desirable to design the surgical access device 10 so that the cannula base 40 is removably and replaceably coupled with both the cannula 60 and the retractor 20. In an exemplary embodiment, all mating connections form a fluid-tight seal. Alternatively, or in addition, one or more seals can be used in conjunction with mating two components. The embodiments disclosed herein can improve the retention of the surgical access device 10 so that it can more easily remain in a desired location and counteract forces attempting to dislodge the device 10 from the incision 104, for instance, forces resulting from insufflation.

Each of the components of the surgical access device 10 can have a variety of configurations. The retractor 20 can be generally configured to be disposed within an incision 104 formed through tissue 102 to form a working channel extending into a body cavity. While the retractor 20 can have a variety of shapes, depending at least in part on the size of the incision in which it will be disposed, the amount of the retractor 20 that will be disposed in the tissue, the type of surgical procedure it will be used to perform, and the shape of complimentary components of the device 10, in one exemplary embodiment the retractor 20 is an elongate hollow cylindrical member having a proximal portion 22 configured to couple to the cannula base 40 and a distal portion 24 configured to retract tissue 102 away from the incision 104. In some embodiments the retractor 20 can be fully disposed within the tissue, while in other embodiments only portions of the retractor 20 can be disposed within the tissue while other portions extend above and/or below the tissue surface. The retractor 20 can be configured to be generally flexible, and thus can be made from a flexible material, such as a polymer. Examples of flexible materials that can be used to form the retractor include polyisoprene, polyurthethane, and silicone. More than one material can be used for form the retractor 20, and the retractor 20 can include portions that are more rigid than other portions. For example, more rigid portions of a retractor can be made from materials such as polycarbonate, polyester, polyetherimide material, or stainless steel, while more flexible portions can be made from materials such as polyisoprene, polyurthethane, and silicone. One exemplary embodiment of a retractor is disclosed in a co-pending patent application entitled "Retractor with Flexible Sleeve" of Fred Shelton and Chris Widenhouse and filed concurrently with the present application, which is hereby incorporated by reference in its entirety.

The retractor 20 can also come in a variety of shapes and sizes, which can depend at least in part on the size of the incision in which it will be disposed, the amount of the retractor 20 that will be disposed in the tissue, the type of surgical procedure it will be used to perform, and the shape of complimentary components of the device 10. For example, the distal portion 24 can be configured to engage tissue 102 located at a distal end 105 of the incision 104 and to retract the tissue 102 away from the incision 104 to form a pathway therethrough. By allowing at least a portion of the retractor 20 to fully pass through the incision 104, the surgical access device 10 is less likely to be affected by the potential collapse of tissue around the cannula connected to the retractor 20, or to a cannula base connected to the retractor 20. Accordingly, instruments passing therethrough are also less likely to be affected by any potential of tissue collapse. For example, if the retractor 20 is disposed through an abdominal wall, the fascia layer can be retracted to prevent the collapse of the fascia around the cannula 60.

The size of the retractor 20 can also be different at the proximal and distal portions 22, 24, or alternatively, the size of each the proximal portion 22 and the distal portion 24 can be substantially similar. In the embodiment shown in FIG. 1, the proximal portion 22 has a constant diameter, and the distal portion 24 expands radially outward to form a flange with a maximum diameter that is greater than a diameter of the proximal portion 22. This is because the retractor 20, in this embodiment, is not fully disposed within the tissue 102. In particular, the proximal portion 22 terminates within the incision 104 while the distal portion 24 extends just beyond the inner surface of the tissue 102 such that the radial flange abuts and engages the inner wall of the tissue. In an exemplary embodiment, the diameters of the proximal and distal portions 22, 24 of the retractor 20 can be approximately in the range of 0.5 to 5 cm. In one exemplary embodiment a maximum diameter of the flange of the distal portion 24 is approximately twice as large as a diameter of the proximal portion 22. However, the size of any portion of the retractor 20, or any other portion of the surgical device 10 for that matter, can be adjusted based at least on the intended use of the device 10.

As further shown in FIG. 1, the distal portion 24 of the retractor can also include features to help retain the retractor 20 in a desired location and to provide stability of the device within the incision 104. For example, the distal portion 24 can include a ring having a diameter that is greater than a diameter of the proximal portion 22 of the retractor 20. The ring of the distal portion 24 can be formed integrally with or disposed within the maximum diameter of the radial flange.

The proximal portion 22 of the retractor 20 can be configured in a variety of ways, but is generally configured to mate to a variety of cannula bases having different configurations, such as cannula base 40. The mating of the retractor 20 and the cannula base 40 will be discussed in more detail below. The proximal portion 22 can also be adjustable and can be configured to control a depth of the retractor 20, for instance when it is disposed in a tissue incision. The proximal portion 22 can also prevent the retractor 20 from becoming fully-pressed through a tissue wall, for instance when the retractor 20 is disposed in an abdominal wall.

The retractor 20 can be coupled with the cannula base 40 to form a working channel extending into a body cavity. The cannula base 40 can generally be configured to receive a cannula therethrough, which in turn can be used to access a surgical site. The cannula base 40 can have many shapes and sizes and can be made from a variety of materials. In the illustrated embodiment a proximal portion 42 of the cannula base 40 is substantially funnel-shaped, and a distal portion 44 is generally cylindrical. The shape of the proximal portion 42 of the cannula base 40 can be generally configured to cooperate with the shape of a proximal portion 62 of the cannula 60, while the shape of the distal portion 44 of the cannula base 40 can be generally configured to cooperate with the shape of the proximal portion 22 of the retractor 20. Thus, a size of the cannula base 40 can generally compliment a size of one or both of the retractor 20 and the cannula 60. In one exemplary embodiment, a maximum diameter of the proximal portion 42 is approximately in the range of 2 to 5 cm, and more particularly approximately in the range of 3 to 4 cm, while a maximum diameter of the distal portion 44 is approximately in the range of 0.5 to 2.5 cm. Of course, the size of any portion of the cannula base 40 can be adjusted based at least on the intended use of the device 10.

A number of different materials can be used to form the cannula base 40. In one embodiment the proximal portion 42 of the cannula base 40 is substantially rigid to provide a sturdy base for receiving the cannula 60. Portions of the cannula base 40 can be more flexible than other potions. For example, the distal portion 44 can be more flexible than the proximal portion 42 to assist with insertion into a retractor. In some embodiments the cannula base 40 can be made from multiple materials to allow portions of the cannula base 40 to have different characteristics. For example, the proximal portion 42 can be made of a substantially rigid material and the distal portion 44 can be made from a more flexible material. In one exemplary embodiment the proximal portion 42 is made of a more rigid material, such as polycarbonate, polyester, polyetherimide material, or stainless steel, and the distal portion 44 is made of a more flexible material, such as polyisoprene, polyurthethane, or silicone. In other embodiments the entire cannula base 40 is made of materials like polycarbonate, polyester, polyetherimide material, or stainless steel. In still other embodiments the entire cannula base 40 is made of a polymer providing sufficient rigidity at the proximal portion 42.

In addition to being configured to receive a cannula, the proximal portion 42 of the cannula base 40 can also be configured to assist the retractor 20 in providing retention and stability of the surgical device 10. For example, the proximal portion 42 can help control the insertion depth of the cannula base 40, and thus the retractor 20 when coupled thereto, to prevent either from being pressed fully through the tissue wall. In one embodiment the proximal portion 42 includes a flange 58 that is configured to engage the outer surface of the tissue located at a proximal end 103 of the incision 104. The flange 58 can include gripping features that allow the cannula base 40 to attach to the tissue 102 without the assistance of an outside component, such as sutures. Some non-limiting examples of gripping features include raised areas, texturized areas, and combinations thereof. In an alternative embodiment an outside component, such as one or more sutures, can be used to help attach the cannula base 40 to the tissue 104. FIGS. 3 and 5-7, which are described in greater detail below, illustrate embodiments in which sutures can be used as part of the cannula 60 or cannula base 40.

The cannula 60 can be disposed in a working channel formed by the cannula base 40 and the retractor 20, and it can provide access to the surgical site therethrough. Similar to the other components of the surgical access device 10, the cannula 60 can have a wide variety of configurations, shapes, and sizes, which are often complimentary to the configurations, shapes, and sizes of the other components of the device 10. In one exemplary embodiment of a cannula, as shown in FIG. 1, a proximal portion 62 of the cannula 60 is substantially funnel-shaped and decreases in diameter distally, and a distal portion 64 of the cannula 60 includes one or sealing passageways or channels 70 extending distally toward a surgical site. Disposed between the proximal and distal portions 62, 64 of the cannula 60 can be a connecting region 63 that is configured to assist with coupling the cannula 60 to the cannula base 40, or the retractor 20 in certain embodiments. As shown, the connecting region 63 is substantially cylindrical.

The shape of the proximal portion 62 of the cannula 60 can be generally configured to compliment the shape of the proximal portion 42 of the cannula base 40. The shape of the connection region 63 of the cannula 60 can be generally configured to compliment the mating features of the mating component (e.g., the cannula base 40 and/or the retractor 20 as desired). The shape of the distal portion 64 of the cannula 60 can be generally configured to allow access to a surgical site. In one exemplary embodiment, a diameter of the proximal portion 62 is approximately in the range of 3 to 5 cm, and a diameter of the connecting region and of the distal portion, the latter defined as a distance d in FIG. 1, is approximately in the range of 0.5 to 2 cm. Similar to the other components of the device, the size of any portion of the cannula 60 can be adjusted based at least on the intended use of the device 10.

The cannula 60 can be made from a variety of materials, including any number of polymers, including but not limited to, polycarbonate, polyester, polyetherimide material, and stainless steel. Further, similar to the cannula base 40, a number of different materials can be used to form the cannula 60 and various portions of the cannula 60, and even the individual channels 70 themselves, can be made from different materials. In one embodiment polytetrafluoroethylene stiffening tubes are provided in at least one of the channels 70 to provide strength and rigidity and to reduce friction. The components of the surgical device 10, however, can also assist with improving the performance of the cannula 60. For example, the retractor 20 and cannula base 40 can help prevent tissue from collapsing around the channels 70 of the cannula 60 when the device 10 is in use. When the surgical device 10 is disposed in an abdomen, the retractor 20 can prevent the fascia layer from collapsing around the channels 70, and thereby the instruments, to avoid restricting and inhibiting the motion of the instruments.

The proximal portion 62 of the cannula 60 can include an opening 66 configured to receive one or more surgical instruments. The proximal portion 62 can also include a flange 72, which can perform in a manner similar as the flange 58 of the cannula base 40 in certain embodiments. For example, the flange 72 can include gripping features, such as raised areas, texturized areas, and other gripping features that assist in engaging tissue without the need for an outside component, such as sutures. The opening 66 of the proximal portion 62 can be in communication with the channels 70 or passageways of the distal portion 64. The illustrated embodiment includes three channels 70, although only two are visible. In other embodiments the cannula 60 can have one, two, three, or more than three separate and distinct channels 70.

The size and shape of the channels 70 can also vary, based at least in part on the various instruments that will be used in conjunction with the cannula 60. The channels 70 can be configured to receive one or more instruments to be used at a surgical site. In one embodiment the channels 70 are flexible, elongate channels that extend in a distal direction. While the channels can have a variety of sizes, in one embodiment the channels 70 have diameters approximately in the range of 5 to 10 mm. The channels 70 can include a seal that is configured to prevent fluid from passing between the surgical site and the cannula 60. A variety of seal types can be used. For example, the seal can be disposed inside a channel 70. Alternatively, a distal end of the channel 70 can include a slit that forms a seal around the instrument(s). A person skilled in the art will recognize that a seal can be formed and/or located anywhere within or around the channel 70. A variety of sealing elements exist, but in one embodiment each channel 70 includes an instrument seal that forms a seal around an instrument disposed therethrough, but otherwise does not form a seal when no instrument is disposed therethrough; a channel seal that forms a seal when no instrument is inserted therethrough; or a combination seal that both seals the channel when no instrument is inserted therethrough and that forms a seal around an instrument inserted therethrough. Exemplary seals include, by way of non-limiting example, duckbill seals, cone seals, flapper valves, gel seals, diaphragm seals, lip seals, iris seals, etc. A person skilled in the art will further appreciate that any combination of seals can be included in any of the disclosed embodiments.

Not only can particular channels be configured to have particular seals, but particular channels can also be configured to receive particular types of instruments. For example, in one embodiment one channel can have a larger diameter such that it is configured to receive an endoscope while the other two can have a wider and deeper entrance space for receiving other surgical instruments. The wider and deeper entrance space can increase the range of motion for any instrument inserted therein and can make working with multiple instruments easier. Non-limiting examples of channels of a cannula, and features that can be incorporated into cannulas and channels thereof, such as venting and insufflation ports, are described in U.S. Patent Application No. 2006/0247673 entitled "Multi-port Laparoscopic Access Device" of Voegele et al. and filed Nov. 2, 2006, and U.S. patent application Ser. No. 12/242,765 entitled "Surgical Access Device" of Widenhouse et al. and filed Sep. 30, 2008, both of which are incorporated by reference in their entireties.

The three general components of the surgical access device 10, i.e., the retractor 20, the cannula base 40, and the cannula 60, can be mated in a variety of ways. As illustrated, a proximal portion 22 of the retractor 20 can be configured to couple to a distal portion 44 of the cannula base 40. While the retractor 20 and cannula base 40 can be coupled together using a variety of coupling techniques, in the illustrated embodiment the proximal portion 22 of the retractor 20 can engage the distal portion 44 of the cannula base 40 by way of a snap-fit. More particularly, the cannula base 40 can include a groove 48 configured to receive a flange 23 of the proximal portion 22 of the retractor 20 to form a sealed mating connection therebetween. The proximal portion 22 can also or alternatively have a size that is slightly larger than a size of the distal portion 44 of the cannula base 40 to allow the proximal portion 22 to be disposed over the distal portion 44, thereby providing for an interference fit. In other embodiments, as indicated above, the cannula base 40 can be configured to be integrally formed with the retractor 20 to form a single cannula support unit. Further, many of the coupling mechanisms discussed below with respect to the cannula base 40 and the cannula 60 can be used with the retractor 20 and the cannula base 40.

The connection between the cannula base 40 and the retractor 20 can generally form a fluid-tight, i.e., sealed, configuration to limit or prevent fluid from passing therebetween. In alternative embodiments the cannula base 40 and the retractor 20 can be integrally formed so as to form a single cannula support unit configured to receive and support the cannula 60. In non-integrally formed embodiments, a variety of different sealed configurations can be formed between the cannula base 40 and the retractor 20, some of which will be described in more detail below with respect to various embodiments. In an embodiment in which the retractor 20 is only partially disposed through an incision extending through tissue, the cannula base 40 can be disposed in the remaining portion of the tissue incision, as illustrated in FIG. 1 with respect to incision 104. In other words, the portion of the retractor 20 positioned in the tissue 102 can have a length that is less than a thickness of the tissue 102 such that the retractor 20 does not extend through the entire thickness of the tissue 102. The cannula base 40, however, can extend through the remaining thickness of the tissue 102 so that the retractor 20 and cannula base 40 combined form a pathway extending through the entire thickness of the tissue 102.

Figure 2:
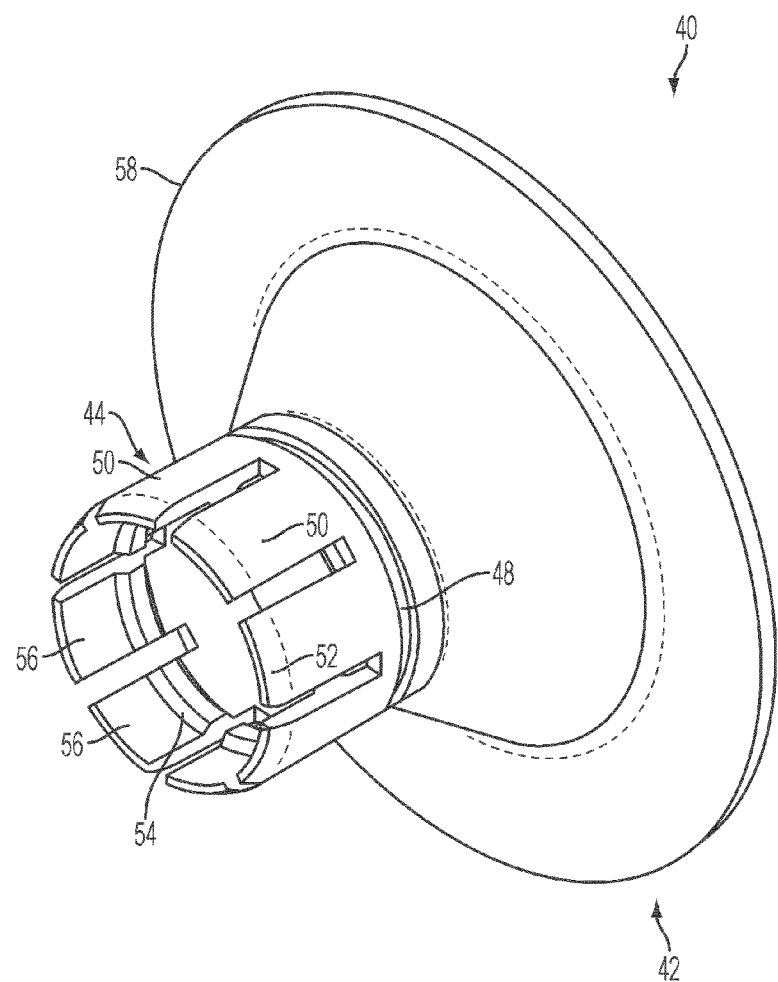
FIG. 2 is a perspective view of a base of the surgical access device of FIG. 1.

A number of features can be included to assist with the insertion of the cannula base 40 into the retractor 20. For example, the distal portion 44 can include a plurality of serrations or axial cut-outs 50 that can provide flexibility, as shown in FIG. 2. The distal portion 44 can also include a chamfered portion 52 that makes the insertion of the cannula base 40 into the retractor 20 easier. In the illustrated embodiment the distal portion 44 also contains a ring 54 disposed on an inner surface 56 of the distal portion 44 of the cannula base. The ring 54 can be used as a feature to assist in mating the cannula 60 to the cannula base 40, as described in more detail below. Although in the illustrated embodiment the entire distal portion 44 of the cannula base 40 extends into the proximal portion of the retractor 20, in other embodiments only the distal-most end or only a portion of the distal portion 44 of the cannula base can couple to the retractor 20.

While the cannula base 40 can be configured to couple to retractors 20 that are either partially or fully disposed in tissue, in some embodiments in which the retractor 20 is fully disposed through tissue, the cannula base 40 can be configured to couple to the proximal portion 22 of the retractor 20 outside of the lumen. Examples of these types of embodiments are described in greater detail below with respect to FIGS. 16 and 19. In such embodiments features previously described as having been useful for inserting the cannula base 40 into the retractor 20 can be used to assist with inserting the cannula 60 into the retractor 20, such as serrations, axial cut-outs, and/or chamfered portions. Even when configured to be located fully outside of the incision, the cannula base 40 can still be configured to be removably and replaceably coupled to each of the retractor 20 and the cannula 60, and likewise can be configured so that a seal can be formed or included between the cannula base 40 and each of the retractor 20 and the cannula 60.

The cannula base 40 can also be configured to mate with the cannula 60. In particular, the cannula 60 can be both removably and replaceably coupled to the cannula base 40. As will be described in greater detail below, the mating features of the cannula 60 can come in many forms, including as described with respect to the illustrated embodiments herein, an interference fit, snap-fit, and/or male and female features, such as threaded sections, pins and receiving portions, tabs and receiving portions, and an annular flange and receiving portions. The connection between the cannula 60 and the cannula base 40 can generally form a fluid-tight, i.e., sealed, configuration, or a seal can be included or formed therebetween. The seal can limit or prevent fluid from passing between the cannula base 40 and the cannula 60.

A variety of different sealed configurations will be described with respect to the various embodiments illustrated herein. In the illustrated embodiment of FIG. 1, two different seals are formed. As shown, the distal portion 64 of the cannula 60 includes a groove 76 which cooperates with the ring 54 of the cannula base 40 to form a sealed, interference fit between the cannula 60 and the cannula base 40. This configuration allows the cannula 60 to be able to snap into and out of the cannula base 40. In alternative embodiments the cannula 60 and the cannula base 40 can be integrally formed to form a single cannula unit. In such embodiments the cannula unit can be removably and replaceably coupled to the retractor 20. A seal is also formed between an inner surface 46 of the proximal portion 42 and the proximal portion 62 of the cannula 60. The inner surface 46 is substantially flat and coincides with an outer surface 68 of the cannula 60 to form a seal therebetween. In an alternative embodiment the inner surface 46 of the cannula base 40 can include protruding or embedded features that coincide with embedded or protruding features of the outer surface 68 of the cannula 60 to form a seal therebetween. The inner surface 46 can also be configured to stop the cannula 60 such that the cannula 60 cannot continue to travel in a distal direction D at a desired stop location. This stop can be created, for example, by contouring the geometries of the cannula base 40 and the cannula 60 accordingly.

The removable and replaceable nature of the retractor 20, cannula base 40, and cannula 60 allows multiple configurations of the same component to be coupled to the same mating component. Thus, one or more configurations of cannula bases can be configured to couple to the same retractor, or the same cannula base can be configured to couple with multiple retractors. Likewise, one or more configurations of cannulas can be configured to couple with the same cannula base, or the same cannula can be configured to couple with multiple configurations of cannula bases. As will be described in greater detail below, the mating features of the cannula base 40, as well as the mating features of the retractor 20 and the cannula can come in a myriad of forms. In the illustrated embodiments the removable and replaceable features include interference fits, snap fits, and male and female mating features, such as threaded sections, pins and cut-out portions, tabs and receiving portions, and an annular flange and receiving portions. A person skilled in the art will understand that the mating features can be used interchangeably between the various components of the surgical access device 10.

Figure 3:
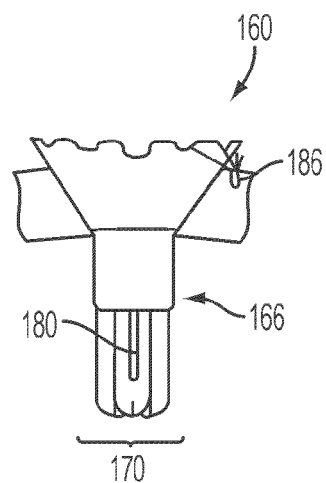
FIG. 3 is a side perspective view of another embodiment of a surgical access device.
Figure 4:
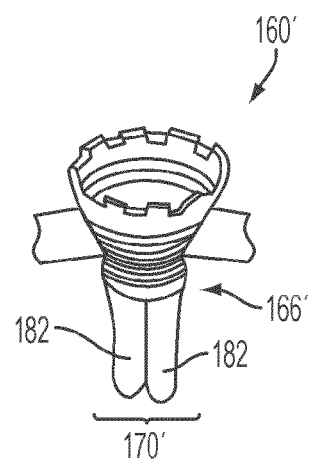
FIG. 4 is a top perspective view of yet another embodiment of a surgical access device.
Figure 5:
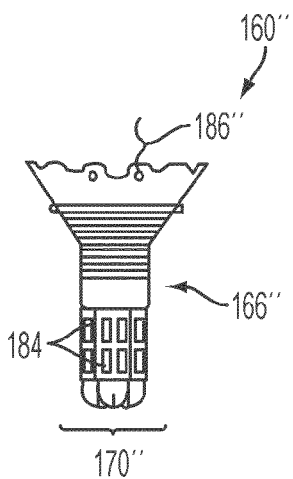
FIG. 5 is a side perspective view of still another embodiment of a surgical access device.

Additional embodiments of surgical access devices are disclosed in FIGS. 3-8. FIGS. 3-5 illustrate embodiments of a cannula 160, 160', 160" for use with surgical access devices in which channels 170, 170', 170" that extend from a distal portion 166, 166', 166" thereof are configured to prevent inversion when an instrument is removed from the channels 170, 170', 170". In particular, each of the channels 170, 170', 170" of the cannulas 160, 160', 160" of FIGS. 3-5 include walls of non-uniform thickness. The thickness can vary throughout the entirety of the cannula 160, 160', 160", or alternatively, only in portions of the cannula 160, 160', 160", for example in only one or more of the channels 170, 170', 170". As illustrated in each of FIGS. 3-5, the channels 170, 170', 170" include features which provide the desired varying wall thickness. In FIG. 3 the channels 170 include axially extending portions 180 that have a different thickness than the remainder of the channel 170. The channel 170 can include any number of axially extending 180, and the portions 180 can be spaced radially around the channel 170 at any distance apart from one another. In FIG. 4 the channels 170' include a length 182 that has a different thickness than the remainder of the channel 170'. In particular, the length 182 is thinner than the other portions of the channel 170'. In FIG. 5 the channels 170" include window portions 184 that have a different thickness than the remainder of the channel 170". In particular, the window portions 184 are thinner than the other portions of the channel 170". In some embodiments the portions 180, 182, and 184 can be generally thinner than the remainder of the channel 170, 170', 170", while in other embodiments the portions 180, 182, and 184 can be generally thicker than the remainder of the channel 170, 170', 170". A person skilled in the art will recognize that other configurations that form a non-uniform wall thickness can also be used.

Further, both FIGS. 3 and 5 illustrate that one or more sutures 186, 186" can be used in conjunction with the cannula 160, 160" to assist in maintaining a location of the cannula 160, 160" and/or a surgical access device associated therewith. FIG. 3 illustrates an embodiment in which the suture 186 is looped around a tab 181 located on a proximal portion 183 of the cannula 160. FIG. 5 illustrates an embodiment in which the suture 186" is threaded through a hole 185 of a proximal portion 183" of the cannula 160". A person having skill in the art will recognize that one or more sutures can likewise be used in conjunction with a cannula base and/or a retractor to assist in maintaining a location of the cannula base, the retractor, and/or a surgical access device associated therewith.

Figure 6:
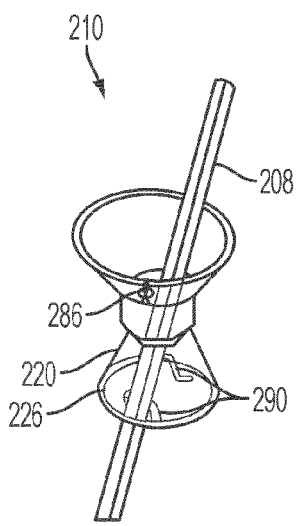
FIG. 6 is a top transparent perspective view of another embodiment of a surgical access device having a retractor that includes at least one hook for receiving an instrument.
Figure 7:
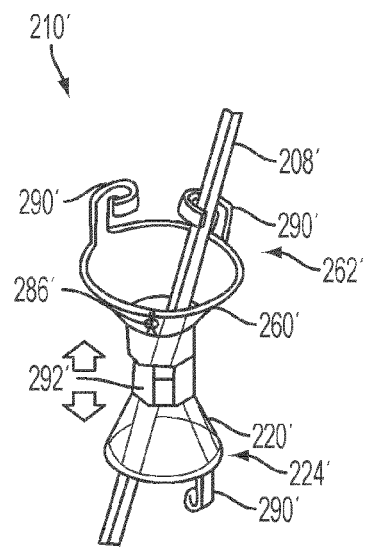
FIG. 7 is a top transparent perspective view of yet another embodiment of a surgical access device having a cannula that includes at least one hook for receiving an instrument.

FIGS. 6 and 7 illustrate two other embodiments of a surgical access device 210, 210'. As shown, the surgical access devices 210, 210' include one or more hooks 290, 290' configured to receive instruments 208, 208'. In FIG. 6 the hooks 290 are disposed on an inner surface 226 of a retractor 220, while in FIG. 7 the hooks 290' are disposed on and can extend proximally from a proximal portion 262' of a cannula 260'. FIG. 7 also illustrates that one or more hooks 290' can be disposed on and can extend distally from a distal portion 224' of a retractor 220'. A person having skill in the art will further recognize that hooks 290, 290' can be disposed in a variety of other locations with respect to the surgical device 210, 210', including as part of a cannula base.

FIGS. 6 and 7 also illustrate that one or more sutures 286, 286' can be used in conjunction with the cannula 260, 260' to assist in maintaining a location of the cannula 260, 260'. FIG. 7 further illustrates including one or more expanding ribs 292' in the surgical access device 210'. As shown, the ribs 292' are disposed between the retractor 220' and the cannula 260' and extend axially therebetween. Any number of ribs 292' can be used, and they can be expanded and contracted as desired, or sized appropriately prior to disposing the device 210' into a tissue incision. When designed to expand and contract, a remote device can be used to actuate expansion and retraction of the ribs 292'. The ribs 292' can be used for thicker tissue. The ribs 292' can provide both added length and stability.

Figure 8:
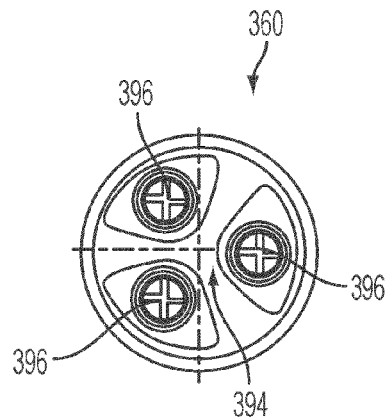
FIG. 8 is a top perspective view of another embodiment of a surgical access device having a cannula with a contoured funnel design.

FIG. 8 illustrates one embodiment of a cannula 360 having a top surface 394 that is scalloped. In particular, a contoured or funneled region surrounds each the access port 396 to help guide instruments into the access ports 396, and thus to the desired location(s) in the working channel. Thus, particularly when a user is unable to see the cannula 360, the contours can help guide the user toward the desired access port 396. In the illustrated embodiment the contours allow for three separate access ports 396 to be easily determined.

The embodiments of FIGS. 9-20 illustrate a variety of different ways in which the components of a surgical access device can be removably and replaceably coupled. Similarly numbered components throughout this specification have generally similar features. A person skilled in the art will recognize that although some of the features that create removable and replaceable coupling will be described with respect to only two components, e.g., the cannula and cannula base, these features can be easily applied to other components, e.g., the cannula base and the retractor or the cannula and the retractor if desired. Likewise, although one component may be described as having a male feature and the component to which it is mated may be described as having a female feature, a person having skill in the art will recognize that the location of the male and female features can be reversed. Similarly, while the embodiments of FIGS. 9-20 have different features for forming a fluid-tight connection or seal, a person having skill in the art will recognize that each of these features can be applied to any embodiment and any component of a surgical access device.

Figure 9:
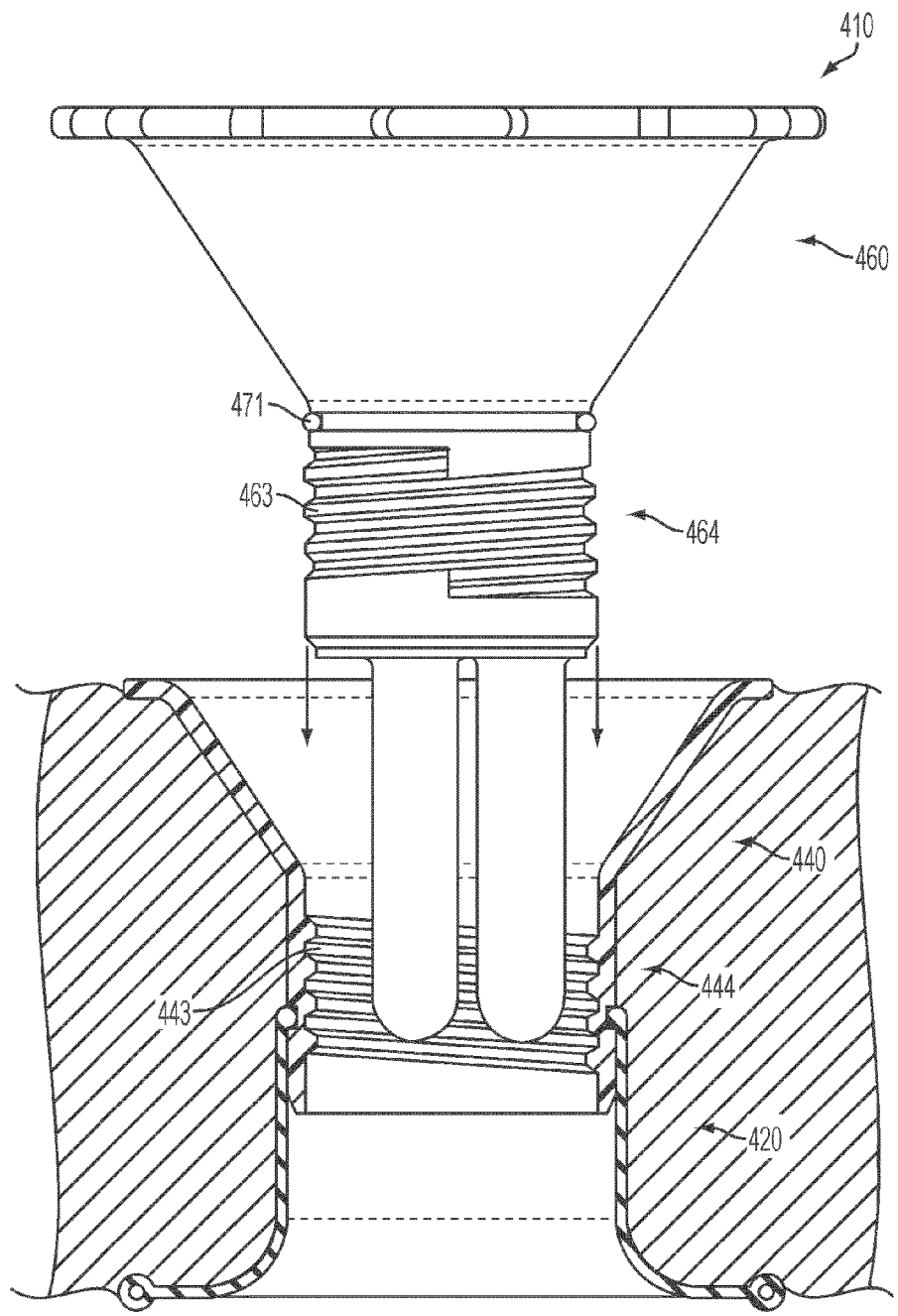
FIG. 9 is a side cross-sectional exploded view of one embodiment of a surgical access device in which a cannula and a base have threaded sections and are uncoupled.
Figure 10:
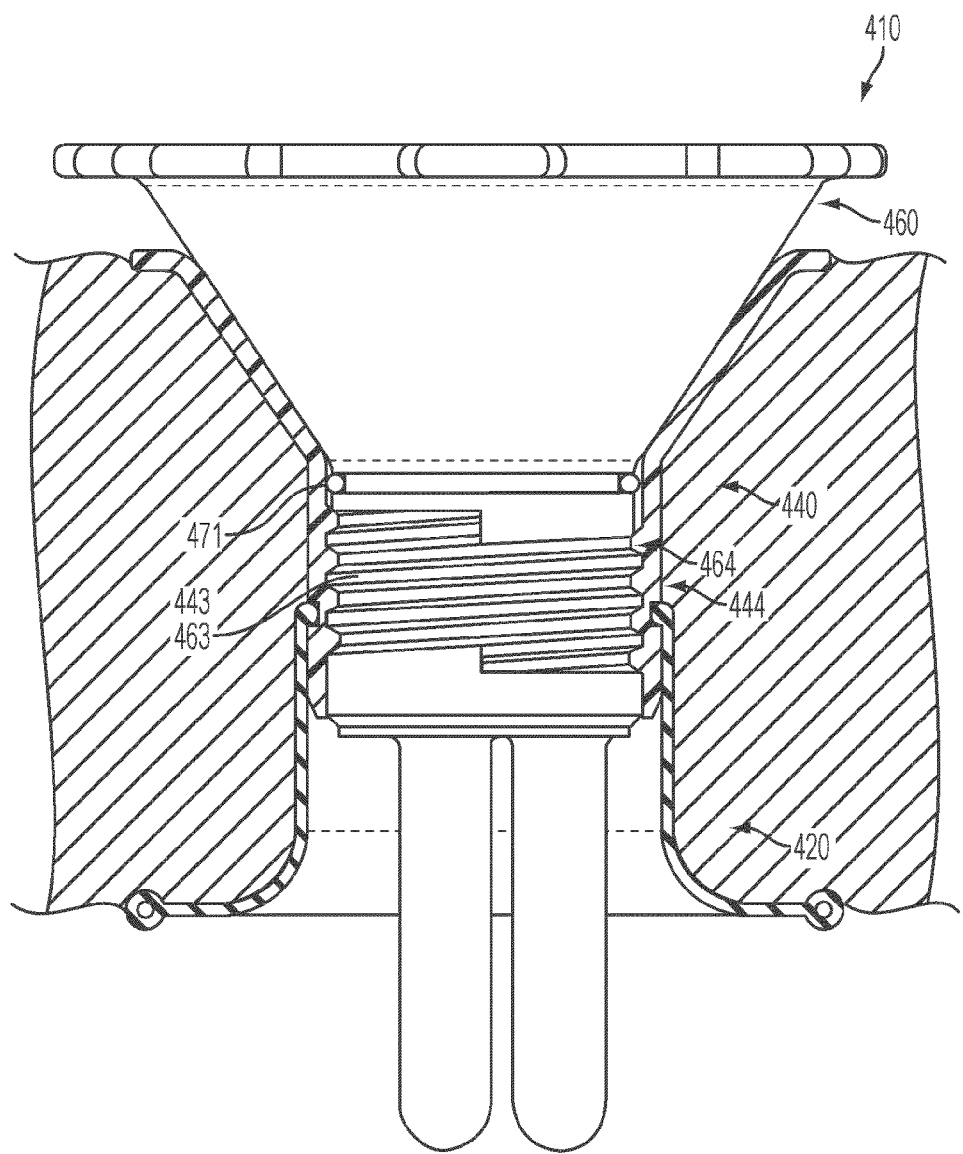
FIG. 10 is a side cross-sectional view of the surgical access device of FIG. 9 with the cannula and base being coupled.

FIGS. 9 and 10 illustrate one embodiment of a surgical access device 410 having a cannula 460, a cannula base 440, and a retractor 420. As shown, the cannula base 440 includes a female coupling mechanism and the cannula 460 includes a male coupling mechanism. More particularly, a distal portion 444 of the cannula base 440 includes an internally threaded section 443 and a distal portion 464 of the cannula 460 includes an externally threaded section 463. The cannula 460 can be screwed into the cannula base 440 by way of the respective threaded sections 463, 443. The cannula 460 can be removed from the cannula base 440 by unscrewing the cannula 460 from the cannula base 440. While the interaction between the threaded sections 443, 463 can create a fluid-tight seal, in one embodiment, as shown in FIGS. 9 and 10, an o-ring 471 is disposed around the cannula 460 to provide an additional seal between the cannula 460 and the cannula base 440.

Figure 11:
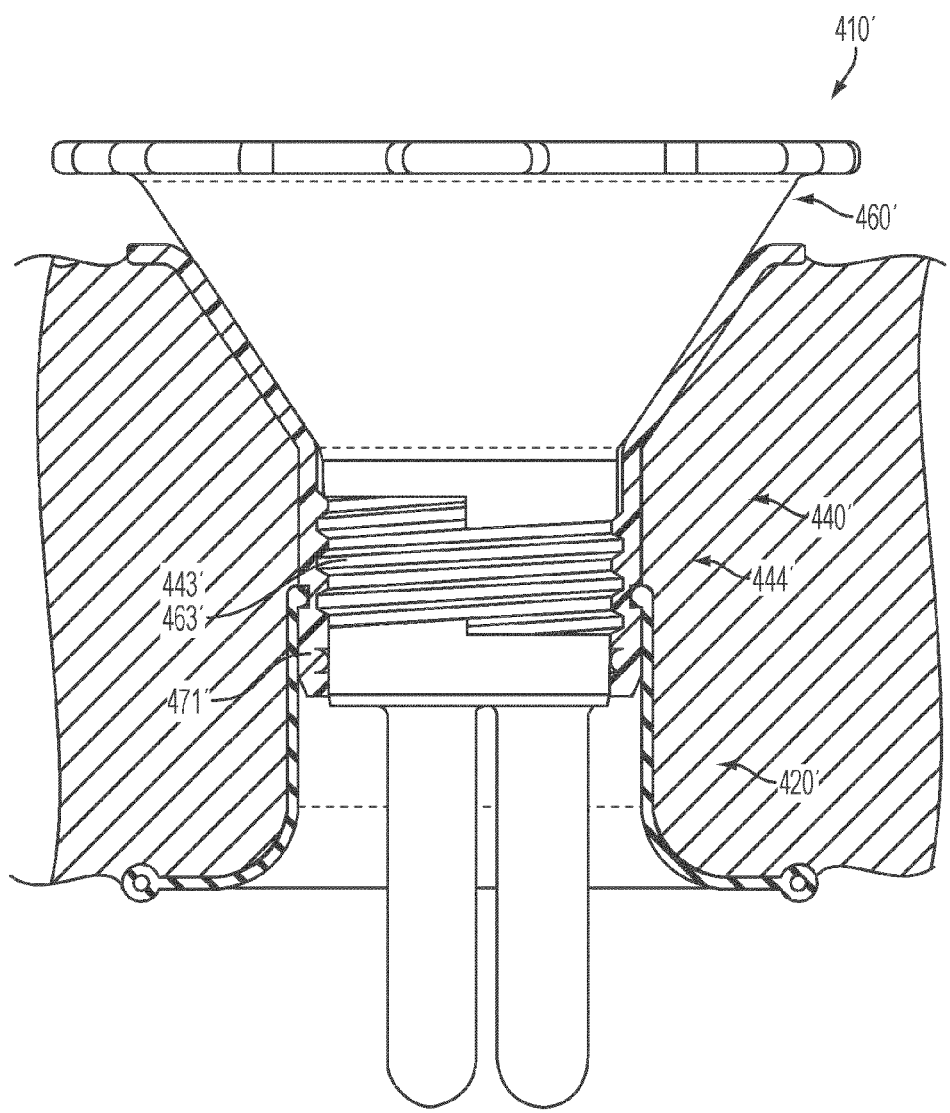
FIG. 11 is a side cross-sectional view of another embodiment of a surgical access device in which a cannula and a base have threaded sections and a seal is disposed at a distal end of the base.

Other forms of seals can also be used. For example, FIG. 11 illustrates an embodiment of a surgical access device 410' having a cannula base 440' and cannula 460' that are threadably coupled in which a seal, shown as an annular ridge 471', is integrally formed as part of the cannula base 440'. In the illustrated embodiment the annular ridge 471' is integrally formed on a distal portion 444' of the cannula base 440', below a threaded section 443', to limit or prevent fluid from passing between the cannula 460' and the cannula base 440' and thus into an opening of a retractor 420' coupled thereto. The annular ridge 471' serves a similar purpose, and functions in a similar manner, as the o-ring 471 of FIGS. 9 and 10. Similar to the embodiment of FIGS. 9 and 10, the cannula 460' can be screwed into the cannula base 440' by way of the respective threaded sections 463', 443'.

Figure 12:
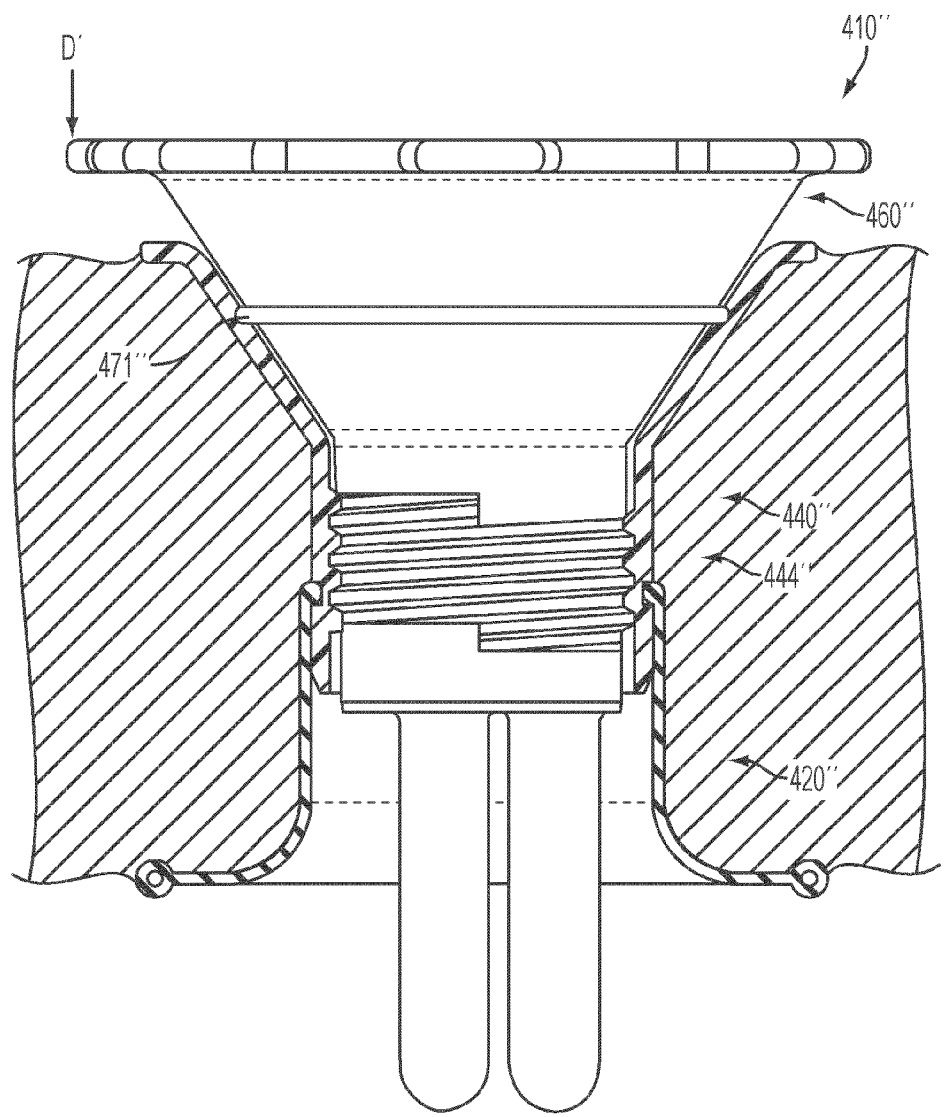
FIG. 12 is a side cross-sectional view of yet another embodiment of a surgical access device in which a cannula and a base have threaded sections and a seal is disposed on the cannula.

In yet another embodiment of a surgical access device 410" having a cannula base 440" and a cannula 460" that are threadably coupled, illustrated in FIG. 12, a seal 471" is integrally formed as part of the cannula 460". As shown, the seal 471" is integrally formed on a funnel-shaped portion of the cannula 460" and is configured to limit or prevent fluid from passing from outside of the cannula base 440" and into a distal portion 444" of the cannula base 440", and thus into an opening of a retractor 420" coupled thereto. Similar to the annular ridge 471', the seal 471" serves a similar purpose and can function in a similar manner as the o-ring 471. Further, the seal 471" can also serve as a stop to prevent further distal movement of the cannula 460" in a distal direction D' toward the cannula base 440". The seal 471" can be disposed to stop the cannula 460" at a desired location to allow for a desired, coupled configuration between the cannula 460" and the cannula base 440".

Figure 13:
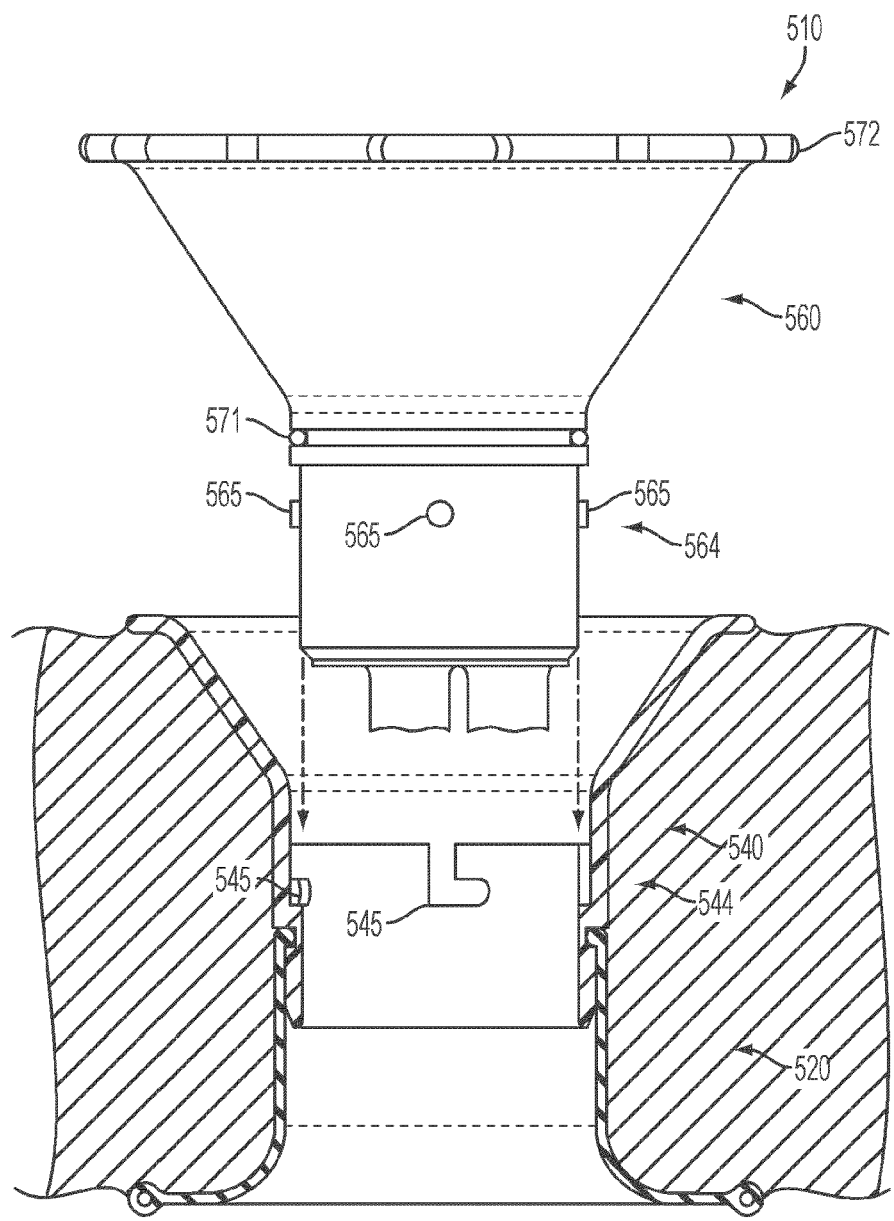
FIG. 13 is a side cross-sectional exploded view of one embodiment of a surgical access device in which a cannula includes at least one pin and a base includes at least one cut-out portion configured to receive the at least one pin.
Figure 14:
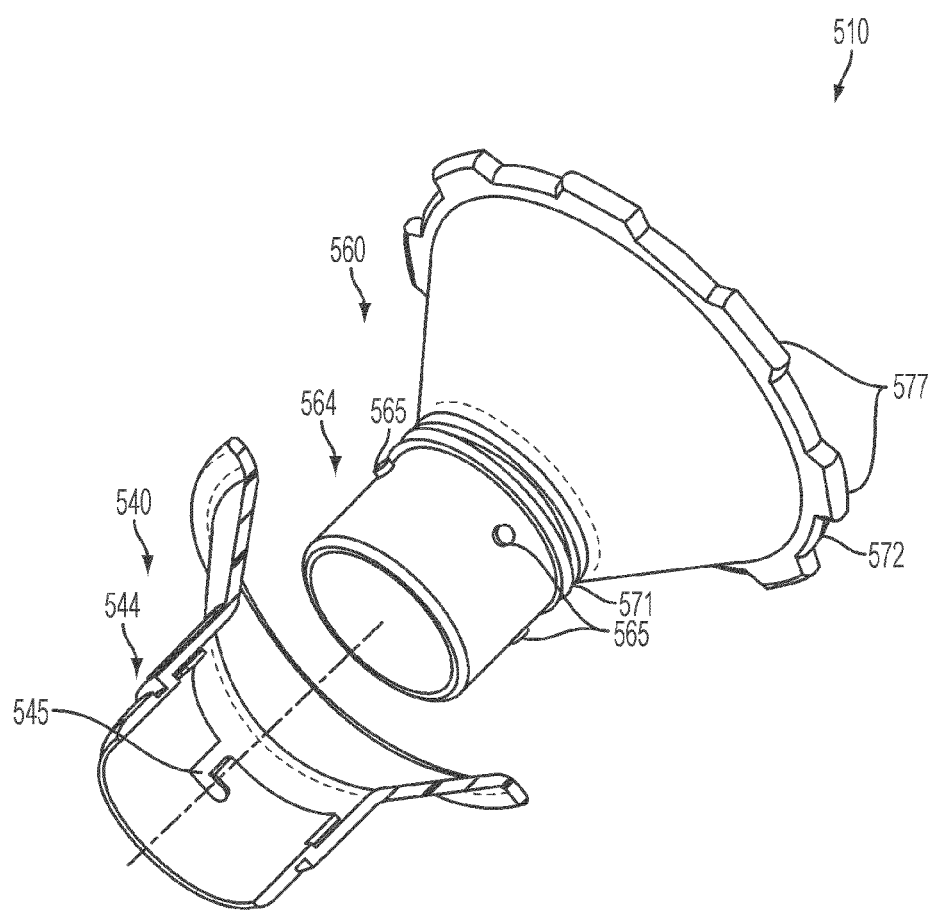
FIG. 14 is a perspective partial cross-sectional exploded view of the surgical access device of FIG. 13.

FIGS. 13 and 14 illustrate another embodiment of a surgical access device 510 having a cannula 560, a cannula base 540, and a retractor 520. As shown, the cannula base 540 includes a female coupling mechanism and the cannula 560 includes a male coupling mechanism. More particularly, a distal portion 544 of the cannula base 540 includes one or more receiving portions, such as keyed cut-out portions 545, for receiving one or more protrusions of the cannula 560. The protrusions of the cannula 560 can be disposed on a distal portion 564 thereof and can be one or more pins 565 or bayonets. In the illustrated embodiment there are four pins 565 and four cut-out portions 545, although any number of pins 565 and cut-out portions 545 can be used. The pins 565 can engage the cut-out portions 545 and be affixed therein to couple the cannula 560 to the cannula base 540. The cannula 560 can be removed by moving the pins 565 out of the cut-out portions 545, following an opposite path as was used to engage the pins 565 with the cut-out portions 545. While the interaction between the pins 565 and cut-out portions 545 can create a seal, in the illustrated embodiment a seal in the form of an o-ring 571 is disposed around the cannula 560 to provide an additional seal between the outside environment and the cannula base 540, and thus an opening of the retractor 520. Further, FIG. 14 also illustrates gripping features 577 on a flange 572 of the cannula 560, which is described with reference to flange 72 of FIG. 1 above.

Figure 15:
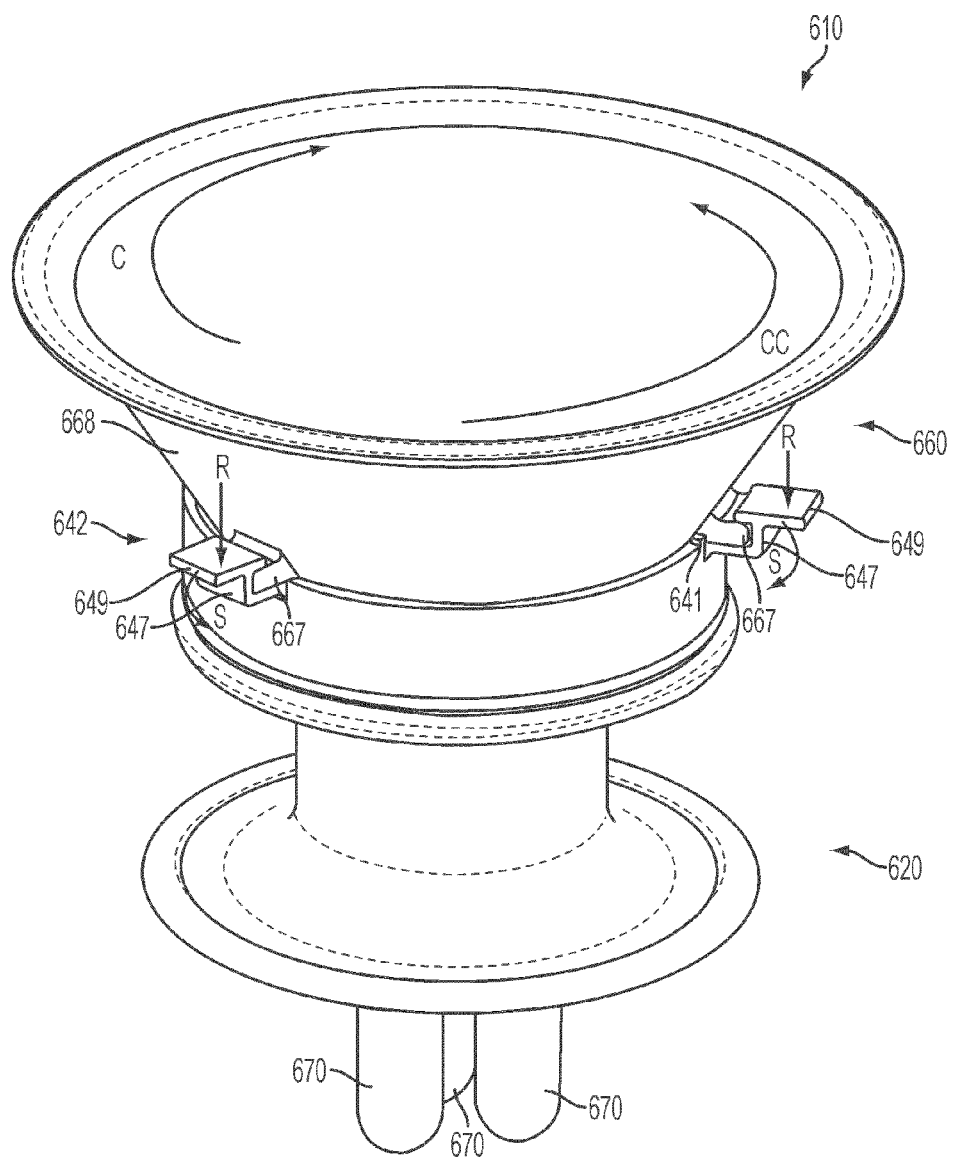
FIG. 15 is a top perspective view of one embodiment of a surgical access device in which a cannula includes at least one tab and a base includes at least one latch configured to receive the at least one tab.
Figure 16:
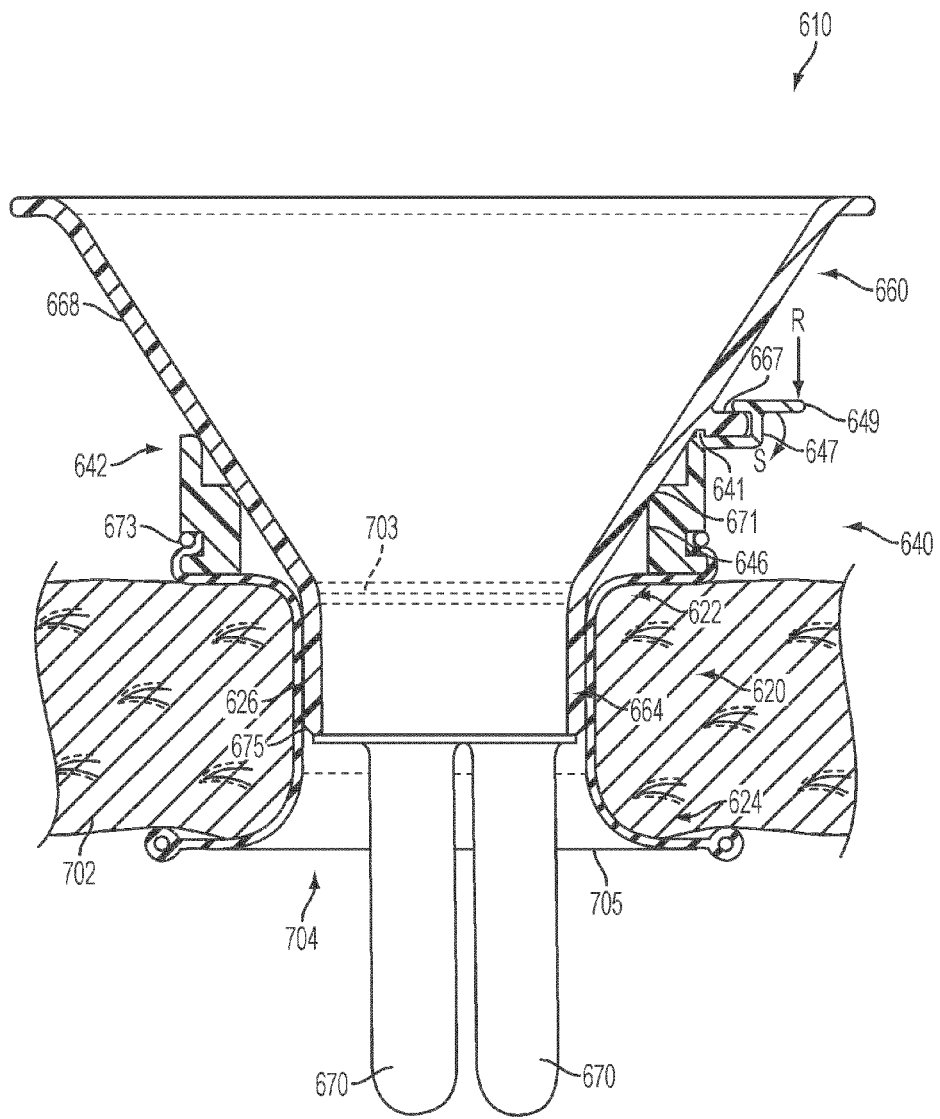
FIG. 16 is a side cross-sectional view of the surgical access device of FIG. 15 with the retractor positioned in tissue.

FIGS. 15 and 16 illustrate yet another embodiment of a surgical access device 610 having a cannula 660, a cannula base 640, and a retractor 620. As shown, the cannula base 640 includes a female coupling mechanism and the cannula 660 includes a male coupling mechanism. More particularly, a proximal portion 642 of the cannula base 640 includes one or more receiving portions in the form of latches 647 for receiving one or more protrusions in the form of tabs 667 of the cannula 660. The tabs 667 of the cannula 660 can be disposed on an outer surface 668 of the cannula 660. In the illustrated embodiment there are three tabs 667 and three latches 647 (only two of which are visible), although any number of tabs 667 and latches 647 can be used. The tabs 667 can slide into the latches 647 in a variety of ways. In the illustrated embodiment the tabs 667 are brought into a similar plane as the latches 647 and then the cannula 660 is twisted in a clockwise direction C to align the tabs 667 and the latches 647. One or more stops 641 can be disposed on the proximal portion 642 of the cannula base 640 to assist in aligning the tabs 667 and the latches 647. The stops 641 can be located such that when the tabs 667 are in contact with the stops 641, the tabs 667 are approximately aligned and fully disposed within latches 647. In the illustrated embodiment each receiving portion 647 includes a stop 641 adjacent thereto, although in other embodiments any number of stops 641, including just one stop 641, can be used.

The cannula 660 can be removed by twisting the cannula 660 out of alignment, as shown in a counter-clockwise direction CC, such that the tabs 667 are not aligned with the latches 647. Alternatively, or in addition, the latches 647 can be flexible such that pressing in a downward direction R on a release 649 of the latch 647 can pivot the release 649 away from the cannula 660 in a direction S, thereby disengaging the latch 647 from the tab 667 of the cannula 660. Thus, the cannula 660 can be removed. While the interaction between the tabs 667 and the latches 647 can create a seal, in the illustrated embodiment a proximal seal 671 is formed between an inner surface 646 of the cannula base 640 and the outer surface 668 of the cannula 660. This is particularly evident in FIG. 16, in which it is shown that the retractor 620 is fully disposed in an incision 704 through tissue 702.

As shown in FIG. 16, a proximal end 622 of the retractor 620 engages tissue 702 located at a proximal portion 703 of the incision 704 and a distal end 624 of the retractor 620 engages tissue located at a distal portion 705 of the incision 704. The cannula base 640 is thus configured to couple to the retractor 620 outside of the lumen 704, as shown by way of an interference fit. More particularly, a proximal end 622 of the retractor 620 has a diameter that is more akin to a diameter of a distal end 624. While in the illustrated embodiment the diameter of the proximal end 622 is a little smaller than the diameter of the distal end 624, in other embodiments the ends 622, 624 have substantially the same diameter, or alternatively, the diameter of the proximal end 622 is larger than the diameter of the distal end 624. A mid-portion 621 of the retractor 620 can extend therebetween, sized to fit in the incision 704, and thus having a diameter smaller than either of the diameters of the proximal and distal ends 622, 624. The proximal end 622 can include an axial extending wall that extends around the cannula base 640 to engage the cannula base 640. While in the illustrated embodiment the connection between the retractor 620 and the cannula base 640 is an interference fit, in other embodiments it can be a snap fit, a male-female connection, or other connections used to couple components together.

A seal, such as o-ring 673, can be disposed between the retractor 620 and the cannula base 640 to limit or prevent fluid from passing therebetween. The cannula 660 couples to and passes through the cannula base 640 and the outer surface 668 of the cannula 660 engages an inner surface 626 of the retractor 620. A seal can be formed between the two surfaces 668, 626, as illustrated, or alternatively a seal can be placed therebetween. Further, as illustrated, a distal portion 664 of the cannula 660 can include chamfers 675, which can aid the insertion of the cannula 660 into the retractor 620. Channels 670 of the cannula 660 can extend beyond the distal end 624 of the retractor 620 and into the body cavity.

Figure 17:
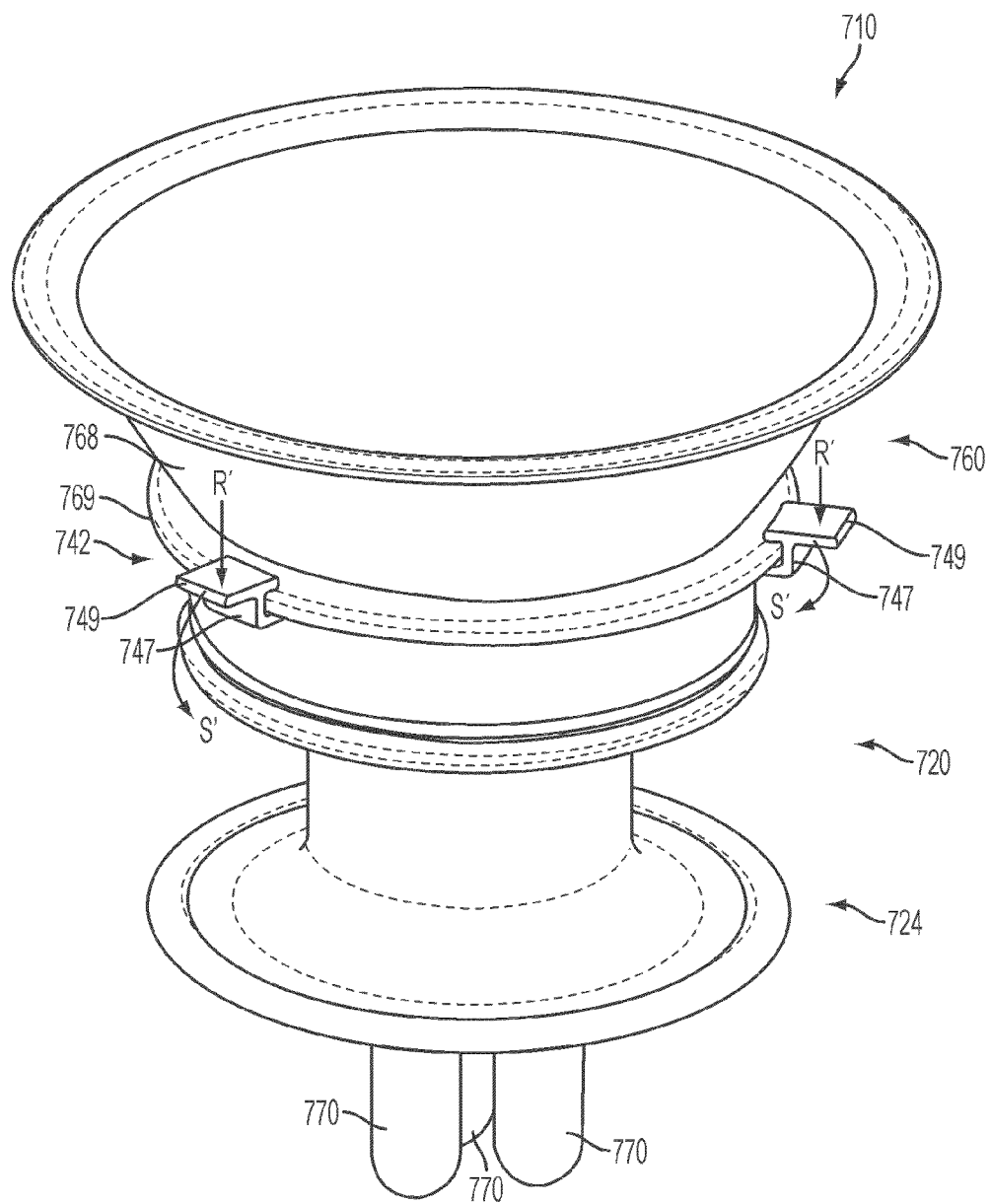
FIG. 17 is a top perspective view of another embodiment of a surgical access device in which a cannula includes an annular flange and a base includes at least one latch configured to receive the annular flange.

FIG. 17 illustrates still another embodiment of a surgical access device 710 having a cannula 760, a cannula base 740, and a retractor 720. As shown, the cannula base 740 includes a female coupling mechanism and the cannula 760 includes a male coupling mechanism. More particularly, a proximal portion 742 of the cannula base 740 includes one or more receiving portions in the form of latches 747 for receiving an angular flange 769 of the cannula 760. The flange 769 can be disposed on an outer surface 768 of the cannula 760. In the illustrated embodiment there are three latches 747 (two of which are visible), although any number of latches 747 can be used. In order to engage the flange 769, releases 749 on the latches 747 can be flexible such that pressing in a downward direction R' on the release 749 can rotate the release 749 away from the cannula 760 in a direction S'. The flange 769 can then be placed in a position in which the latches 747 can engage the flange 769 when the force in the downward direction R' is released. Any number of seals, as described at least with respect to FIGS. 15 and 16 and throughout the application as a whole, can be used in conjunction with this embodiment. The interaction between the flange 769 and the receiving portions 747 can also create a seal. Channels 770 of the cannula 760 can extend beyond a distal portion 724 of the retractor 720.

Figure 18:
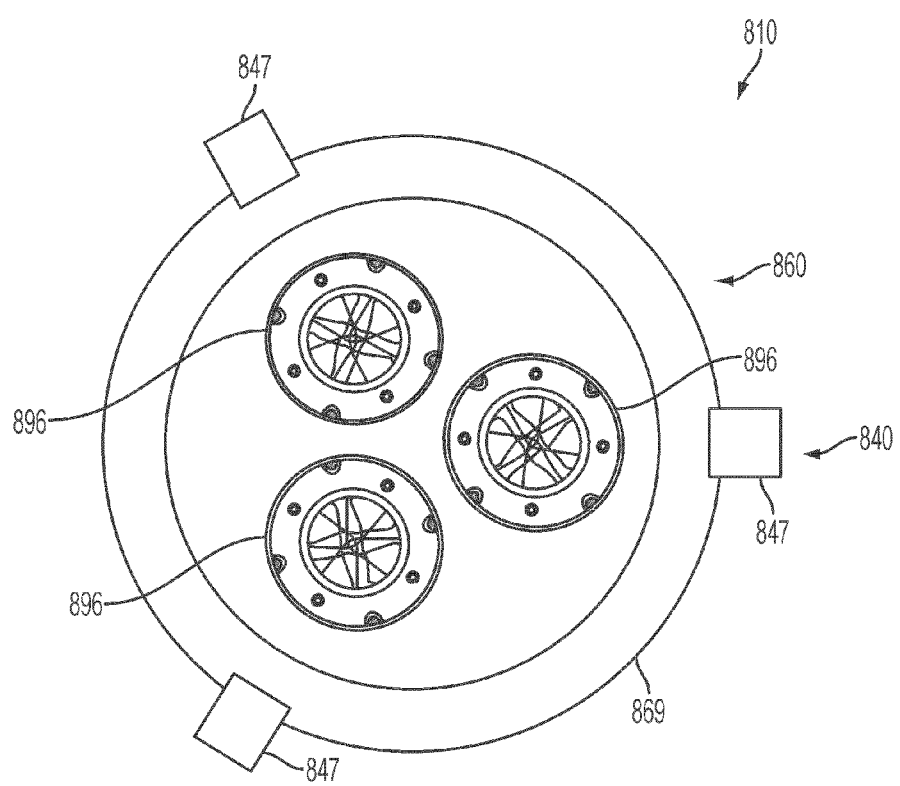
FIG. 18 a top view of yet another embodiment of a surgical access device in which a cannula includes an annular flange configured to be received by at least one latch of a base.
Figure 19:
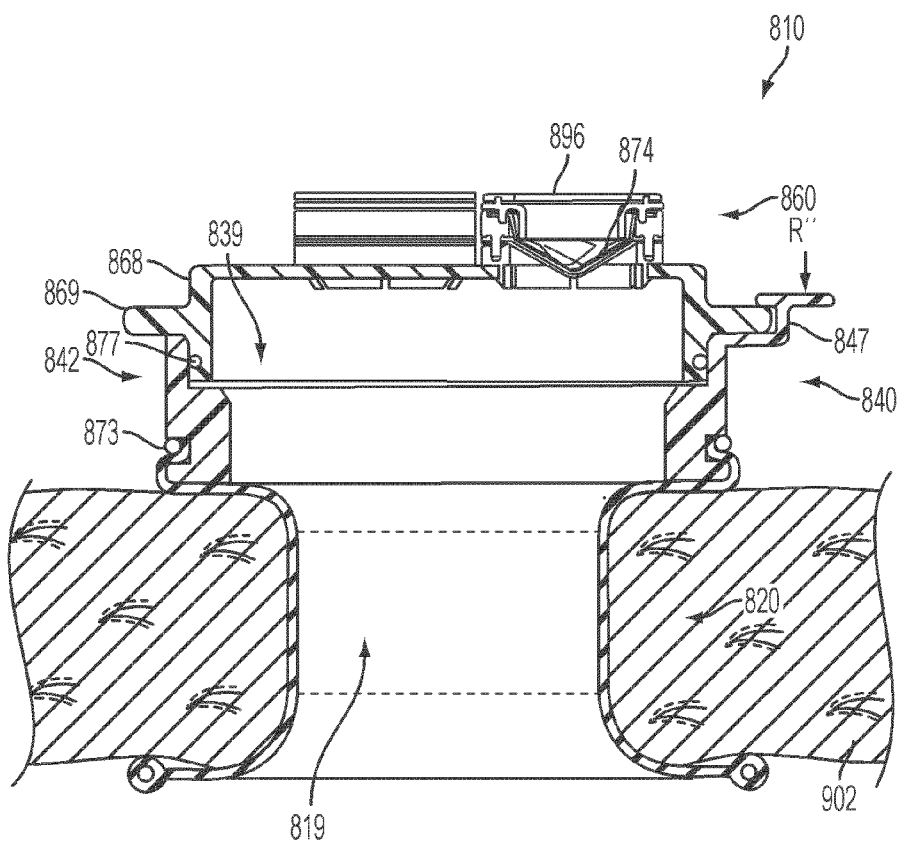
FIG. 19 is a side cross-sectional view of the surgical access device of FIG. 18 with the retractor positioned in tissue and the at least one latch being in a locked position.
Figure 20:
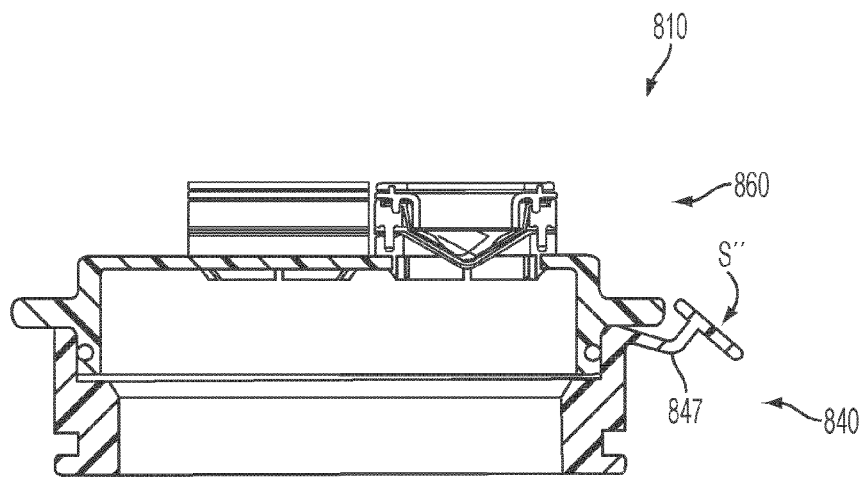
FIG. 20 is a side-cross sectional view of a portion of the surgical access device of FIG. 19 in which the at least one latch is in an unlocked position.

FIGS. 18-20 illustrate another embodiment of a surgical access device 810 having a cannula 860, a cannula base 840, and a retractor 820. The retractor 820 is similar to the retractor 620 of FIGS. 15 and 16 because it is configured to be fully disposed in tissue 902. Similar to the embodiments of the surgical access device 610 of FIGS. 15 and 16, the cannula base 840 is configured to couple to a proximal portion 822 of the retractor 820 by way of an interference fit, and a seal, such as o-ring 873, can be disposed between the retractor 820 and the cannula base 840 to limit or prevent fluid from passing therebetween.

The cannula 860 is configured differently than the cannula 660 of the surgical access device 610 in that rather than including channels 670 for disposing instruments therein, the cannula 860 includes one or more entry ports 896. The entry ports 896 can each include an opening in communication with an opening 839 in the cannula base 840, and thereby an opening 819 in the retractor 820 leading to the surgical site. Similar to the channels 670, the entry ports 896 are sealed to prevent fluid from passing therethrough, such as when instruments are inserted and removed through the cannula 860. In the illustrated embodiment, a duckbill seal 874 is used, but in other embodiments any number or type of seal, including the seals discussed with respect to channels 70 above, can be used. As illustrated, the cannula 860 is configured to seat on the cannula base 840. While it is possible to form a sealed connection based on the coupling of the cannula 860 to the cannula base 840, in the illustrated embodiment a separate seal, such as o-ring 877, can be disposed therebetween to limit or prevent fluid from passing between the cannula 860 and the cannula base 840. When disposing the surgical access device 810 in tissue 902, its configuration is similar to the configuration described with respect to the surgical device 610. The retractor 820 is disposed through the thickness of the tissue 902, and thus the cannula base 840 couples to the retractor 820 outside of the tissue 902.

The coupling mechanisms used in FIGS. 18-20 are similar to the coupling mechanisms of FIG. 17. A female coupling mechanism includes one or more receiving portions in the form of latches 847, as shown three, disposed on a proximal portion 842 of a cannula base 840 and a male coupling mechanism includes an annular flange 869 disposed on an outer surface 868 of the cannula 860. The interaction between the annular flange 869 and the latches 847 is similar to the interaction of the flange 769 and the receiving portions 747 of the device 710 of FIG. 17. Thus, applying a force in a downward direction R", as shown in FIG. 19, can allow the latches 847 to be pivoted away from the cannula 860 in a direction S", as shown in FIG. 20, so that the cannula 860 can be engaged (FIG. 19) and disengaged (FIG. 20) from the cannula base 840.

In use, a surgical access device can enable a user to access a surgical site and work at the surgical site without many of the space, retention, and stability issues that are associated with previous versions of surgical access devices. For convenience, when discussing various methods of using surgical access devices, rather than reciting each of the various embodiments of surgical access devices and their related components, reference will be made to the surgical access device 10 of FIG. 1. When discussing particular types of removable and replaceable coupling features, particular surgical access devices and figures related to the same may be referenced. A person skilled in the art will recognize to the extent that many of these features are interchangeable between embodiments, many of the steps of the methods are likewise interchangeable.

An incision 104 can be formed in a tissue 102 of a body. For example, an incision 104 can be formed in tissue 102, such as an abdominal wall. In order to allow a surgical access device 10 access through the incision 104, a retractor 20 can be positioned in the incision 104. The retractor 20 can form a working channel from outside of the body to the surgical site. More particularly, the retractor 20 can engage the tissue 102 surrounding the opening and retract the tissue 102, including the fascia layer when the surgical site is an abdomen for instance, out of the path formed by the incision 104. In some embodiments the retractor 20 can be disposed partially in the incision 104 such that a distal portion 24 of the retractor 20 is distal of the incision 104 and a proximal portion 22 of the retractor 20 terminates within the tissue (e.g., FIGS. 1 and 9-13), while in other embodiments the retractor 20 is fully disposed through the thickness of the tissue such that the distal portion 24 is distal of the incision 104 and the proximal portion 22 terminates proximal of the incision 104 (e.g., FIGS. 16 and 19). While a retractor can be disposed in an incision in a number of ways, in one embodiment the retractor 20 is folded or collapsed and inserted into and through the incision 104. The distal portion 24 of the retractor 20 can engage an inner surface of the tissue 102 and the remaining portion of the retractor 20 can be pulled back through the tissue 102 to securely engage the retractor 20 at least partially within the incision 104.

The cannula base 40 can be coupled to the retractor 20. In one embodiment the cannula base 40 is coupled to the retractor 20 before either is inserted into the incision 104 (or it is integrally formed therewith), while in another embodiment the cannula base 40 is coupled to the retractor 20 after the retractor 20 is at least partially secured within the incision 104. The cannula base 40 can be coupled to the proximal portion 22 of the retractor 20 so that it extends in a proximal direction from the retractor 20. Generally, when the retractor 20 is not fully disposed through the tissue, the cannula base 40 can be disposed in the remaining portion of the incision 104 and thus will terminate proximate of a proximal portion 103 of the incision 104. In such embodiments the flange 58 can engage the outer surface of the tissue at its proximal portion 103 to assist in creating stable access to the surgical site (e.g., FIGS. 1 and 9-13). In embodiments in which the retractor 20 is fully disposed through the tissue, the cannula base 40 can still be coupled to the retractor 20, as illustrated by FIGS. 16 and 19. Coupling the cannula base 40 to the retractor 20 can be accomplished in any number of ways, including by any of the coupling mechanisms described with respect to FIGS. 9-20 for coupling the cannula 60 to the cannula base 40. Thus, the cannula base 40 and the retractor 20 can at least be coupled by an interference fit, a snap-fit, by way of threaded sections, pins and receiving portions, tabs or an annular flange and receiving portions, and other types of male-female mechanisms. Coupling the cannula base 40 to the retractor 20 can form a fluid-tight seal therebetween.

The cannula 60 can be coupled to the cannula base 40. In one embodiment the cannula 60 is coupled to the cannula base 40 before the cannula base 40 is coupled to the retractor 20, while in another embodiment the cannula 60 is coupled to the cannula base 40 after the cannula base 40 is coupled to the retractor 20. As described with respect to FIGS. 9-20, the cannula 60 and the cannula base 40 can be coupled in any number of manners, including but not limited to an interference fit, a snap-fit, by way of threaded sections, pins and receiving portions, tabs or an annular flange and receiving portions, and other types of male-female mechanisms. Coupling the cannula 60 to the cannula base 40 can form a fluid-tight seal therebetween.

One or more instruments can be inserted through the surgical access device 10 to perform any number of procedures. In embodiments in which the cannula 60 includes a plurality of channels 70, each channel 70 can be configured to receive one or more instruments therein, depending on the desired use or procedure. In some instances, certain channels 70 may be specifically designed for particular uses. Instruments can also be removed from the surgical access device 10. Seals can be disposed in the channels 70 to help limit or prevent unwanted fluid from entering or exiting the surgical site when instruments are inserted and removed from the surgical access device 10.

Not only can instruments be inserted and removed during a surgical procedure, but components of the surgical access device 10 itself can be inserted and removed during a surgical procedure. For example, because the cannula 60 is removably and replaceably coupled to the cannula base 40, the cannula 60 can be decoupled from the cannula base 40 and a second cannula can be coupled to the cannula base 40. The second cannula can have a similar or different configuration than the first cannula 60, depending on the desired use. The second cannula can likewise be removed and other cannulas, including the original cannula 60, can be removably and replaceably coupled to the cannula base 40. Alternatively, after removing the first cannula 60, an object, such as a tissue specimen, a tumor, or other object or specimen located at a surgical site, can be removed from the surgical site and then the first cannula 60, or any other cannula, can be coupled to the cannula base 40. A kit having multiple cannulas, including similar and/or different configurations, can be created as a result of the removable and replaceable nature of the interaction between the cannula and the cannula base. Different cannulas can have different sized channels and/or seals for forming a seal around different sized instruments. A single cannula can have different-sized channels, and/or a single cannula can have the same-sized channels, and the cannulas can be used cooperatively for a procedure. The cannulas of a kit allow for the cannulas to be interchangeably used with a surgical access device.

Likewise, the cannula base 40 can also be removably and replaceably associated with the retractor 20 in a manner similar as described above with respect to the cannula 60 and the cannula base 40. The same or additional cannula bases can be coupled and decoupled from the retractor 20. The cannula base 40 can be removed, an object from the surgical site removed, and then the cannula base 40, or another cannula base, can be coupled to the retractor 20. A kit having multiple cannula bases, including similar and/or different configurations, can be created as a result, and can optionally be combined with a kit having multiple cannulas. The cannula bases of a kit allow for cannula bases to be interchangeably used with a surgical access device. A person skilled in the art will recognize that such kits can also include multiple retractors, including similar and/or different retractors.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
   a cannula having a tapered proximal portion defining only one proximal opening, a cylindrical intermediate portion having a mating feature, and a distal portion comprising a plurality of separate and distinct distal passageways, the only one proximal opening being in direct communication with the plurality of separate and distinct distal passageways;
   a cannula base having a tapered proximal portion on which the proximal portion of the cannula is seated and a cylindrical distal portion having a mating feature that is complementary to the mating feature of the cannula; and
   a retractor directly coupled to and extending distally from the cannula base, the distal portion of the cannula extending through the retractor.

2. The surgical access device of claim 1, wherein the cannula base and the retractor are fixedly coupled to one another.

3. The surgical access device of claim 1, wherein the cannula base and the retractor are removably and replaceably coupled.

4. The surgical access device of claim 3, wherein the cannula base and the retractor form a fluid-tight configuration when coupled together.

5. The surgical access device of claim 1, wherein the retractor is more flexible than the cannula base.

6. The surgical access device of claim 1, wherein the mating feature of the cannula includes a threaded section and the mating feature of the cannula base includes a threaded section, to removably and replaceably couple the cannula to the cannula base.

7. The surgical access device of claim 1, wherein the mating feature of the cannula base includes at least one receiving portion and the mating feature of the cannula includes at least one protrusion configured to extend into and engage the at least one receiving portion to removably and replaceably couple the cannula to the cannula base.

8. The surgical device of claim 1, wherein the retractor includes a distal ring having a diameter greater than a diameter of a proximal portion of the retractor.

9. The surgical device of claim 1, further comprising a plurality of cannulas configured to be removably and replaceably coupled to the cannula base.

10. A surgical access device, comprising:
    a cannula having a proximal end with only one opening extending therethrough and a plurality of elongate flexible channels extending directly from the only one opening in a distal direction, each channel having an opening extending therethrough in direct communication with the only one opening extending through the proximal end of the cannula; and
    a support base having a retractor extending directly from the support base, the support base being configured to removably seat the cannula therein such that the cannula extends through the support base from at least a proximal end on the support base to beyond a distal end of the support base and the plurality of elongate flexible channels extend through the retractor.

11. The surgical access device of claim 10, wherein the support base is removably and replaceably coupled to the retractor.

12. The surgical access device of claim 11, wherein the support base and the retractor form a fluid-tight configuration when coupled together.

13. The surgical device of claim 10, wherein one of the support base and cannula includes a male locking mechanism configured to couple with a female locking mechanism on the other one of the support base and cannula to removably and replaceably couple the cannula to the support base.

14. The surgical device of claim 10, wherein one of the retractor and support base includes a female locking mechanism configured to couple with a male locking mechanism on the other one of the support base and retractor to removably and replaceably couple the support base to the retractor.

15. The surgical device of claim 10, wherein the retractor further includes a distal ring having a diameter greater than a diameter of a proximal portion of the retractor.

* * * * *